US007160892B2

(12) United States Patent
Harada et al.

(10) Patent No.: US 7,160,892 B2
(45) Date of Patent: Jan. 9, 2007

(54) PYRIMIDONE COMPOUNDS AND PHARMACEUTICAL COMPOSITIONS CONTAINING THE SAME

(75) Inventors: Hitoshi Harada, Ibaraki (JP); Osamu Asano, Ibaraki (JP); Masato Ueda, Ibaraki (JP); Shuhei Miyazawa, Ibaraki (JP); Yoshihiko Kotake, Ibaraki (JP); Yasuhiro Kabasawa, Gunma (JP); Masahiro Yasuda, Ibaraki (JP); Nobuyuki Yasuda, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 66 days.

(21) Appl. No.: 10/492,547

(22) PCT Filed: Oct. 22, 2002

(86) PCT No.: PCT/JP02/10953

§ 371 (c)(1),
(2), (4) Date: Apr. 14, 2004

(87) PCT Pub. No.: WO03/035640

PCT Pub. Date: May 1, 2003

(65) Prior Publication Data

US 2004/0259865 A1    Dec. 23, 2004

(30) Foreign Application Priority Data

Oct. 22, 2001    (JP) .............................. 2001-324142

(51) Int. Cl.
*A61K 31/5377*  (2006.01)
*A61K 31/513*  (2006.01)
*C07D 417/02*  (2006.01)
*C07D 413/02*  (2006.01)
*C07D 43/02*  (2006.01)

(52) U.S. Cl. ...................... 514/269; 544/123; 544/295; 544/320; 544/60

(58) Field of Classification Search ............. 514/227.5, 514/235.5, 252.14, 269; 544/123, 295, 60, 544/320
See application file for complete search history.

(56) References Cited

U.S. PATENT DOCUMENTS 4,725,600 A    2/1988    Takaya et al.
6,096,753 A    8/2000    Spohr et al.

FOREIGN PATENT DOCUMENTS

| CN | 1088053 | 6/1994 |
|---|---|---|
| EP | 0 216 247 A2 | 4/1987 |
| EP | 1136482 A1 | 9/2001 |
| EP | 1136486 A1 | 9/2001 |
| JP | 3-173889 A | 7/1991 |
| JP | 4271770 A | 9/1992 |
| JP | 6-211669 A | 8/1994 |
| JP | 11-263789 A | 9/1999 |
| WO | WO 94/16702 A1 | 8/1994 |
| WO | WO 97/33883 A1 | 9/1997 |
| WO | WO 98/24780 | * 6/1998 |
| WO | WO 98/24780 A2 | 6/1998 |
| WO | WO 98/24782 A2 | 6/1998 |
| WO | WO 99/35147 A1 | 7/1999 |
| WO | WO 99/62518 A1 | 12/1999 |
| WO | WO 99/64418 A1 | 12/1999 |
| WO | WO-00/18758 A1 | 4/2000 |
| WO | WO 00/24742 A1 | 5/2000 |
| WO | WO 01/02400 A1 | 1/2001 |
| WO | WO 01/80893 A1 | 1/2001 |
| WO | WO-01/70727 A1 | 9/2001 |

OTHER PUBLICATIONS

Hannah et al, Bioorganic and Medicinal Chemistry, 2000, 8, 739-750.*
Chemical Abstracts, vol. 77, Abstract No. 34471j.
Duncan R. Hannah et al.; Bioorganic & Medicinal Chemistry, vol. 8, No. 4, pp. 739-750, 2000.
Dietrich van Calker et al.; Journal of Neurochemistry, vol. 33, pp. 999-1003, 1979.
Robert F. Bruns et al.; Molecular Pharmacology, vol. 29, pp. 331-346, 1986.
W. Wan et al.; Journal of Neurochemistry; vol. 55, No. 5, pp. 1763-1771, 1990.
Igor Feoktistov et al.; J. Clin. Invest., vol. 96, pp. 1979-1986, 1995.
Alistair K. Dixon et al.; British Journal of Pharmacology, No. 118, pp. 1461-1468, 1996.

(Continued)

*Primary Examiner*—Shaojia A. Jiang
*Assistant Examiner*—Ganapathy Krishnan
(74) *Attorney, Agent, or Firm*—Birch, Stewart, Kolasch and Birch, LLP

(57) ABSTRACT

The invention provides novel pyrimidone compounds exhibiting excellent antagonism against adenosine receptors ($A_1$, $A_{2A}$, and $A_{2B}$ receptors), particularly, compounds represented by the general formula (1), salts thereof, or solvates of both: (1) wherein $R^1$ and $R^2$ are each independently hydrogen, $C_{1-6}$ alkyl, $C_{2-6}$ alkenyl, $C_{2-6}$ alkynyl, $C_{3-8}$ cycloalkyl, $C_{3-8}$ cycloalkenyl, a 5- to 14-membered nonaromatic heterocyclic group, a $C_{6-14}$ aromatic hydrocarbon group, a 5- to 14-membered aromatic heterocyclic group, $C_{1-6}$ acyl, or $C_{1-6}$ alkylsulfonyl; $R^3$ is hydrogen, $C_{1-6}$ alkyl, $C_{2-6}$ alkenyl, or $C_{2-6}$ alkynyl; $R^4$ is a $C_{6-14}$ aromatic hydrocarbon group; a 5- to 14-membered aromatic heterocyclic group, or a 5- to 14-membered nonaromatic heterocyclic group having at least one unsaturated bond; and $R^5$ is a $C_{6-14}$ aromatic hydrocarbon group or a 5- to 14-membered aromatic heterocyclic group (with the proviso that every group except hydrogen may be substituted).

19 Claims, No Drawings

OTHER PUBLICATIONS

Julie A. Peachey et al.; Naunyn-Schmiedeberg's Arch Pharmacol., No. 359, pp. 140-146, 1999.
Makoto Kadowaki et al.; British Journal of Pharmacology, No. 129, pp. 871-876, 2000.
Maarten de Zwart et al.; Drug Development Research, No. 48, pp. 95-103, 1999.
Yong-Chul Kim et al.; J. Med. Chem., No. 43, pp. 1165-1172, 2000.
Bioorg. Med. Chem., vol. 8, No. 4, pp. 739-750 (2000).
Chemical Abstracts, vol. 77, abs. No. 34471, RN=37005-17-7, 37012-54-7.
Kadowaki et al., British Journal of Pharmacology, vol. 129, pp. 871-876 (2000).
Nitahara et al., Neuroscience, vol. 67, No. 1, pp. 159-168 (1995).
Peachey et al., Naunyn-Schmiedeberg's Arch Pharmacol., vol. 359, pp. 140-146 (1999).
Tomaru et al., European Journal of Pharmacology, vol. 264, pp. 91-94 (1994).
Christofi et al., Gastroenterology, vol. 104, pp. 1420-1429 (1993).
Suzuki et al., Jpn. J. Pharmacol., vol. 68, pp. 119-123 (1995).
Dixon et al., British Journal of Pharmacology, vol. 118, pp. 1461-1468 (1996).
Klauser et al., Pharmacology, vol. 47, Supp. 1, pp. 256-260 (1993) (Abstract).
Skulnick et al., J. Med. Chem. vol. 28, pp. 1864-1869, (1985).
Kabbe et al., Liebigs Ann. Chem., vol. 704, pp. 144-149, (1967).

\* cited by examiner

PYRIMIDONE COMPOUNDS AND PHARMACEUTICAL COMPOSITIONS CONTAINING THE SAME

FIELD OF THE INVENTION

The present invention relates to a novel pyrimidone compound, a production process thereof, and a pharmaceutical preparation containing it and use thereof.

PRIOR ART

Adenosine is an important regulatory factor involved in many intracellular metabolisms in the living body, such as regulation of energy levels and cAMP (cyclic adenosine monophosphate) levels, opening and closing potassium channels, and inflow of calcium ions into cells, and its interaction with G protein-coupled adenosine receptors on the surface of a cell is essential for exhibiting these physiological activities.

Adenosine receptors were classified under two subtypes, $A_1$ receptor and $A_2$ receptor based on the involvement in adenylate cyclase (J. Neurochem., Vol. 33, p 999–1003, (1979)), and thereafter, the $A_2$ receptor has been classified under two subtypes, $A_{2A}$ and $A_{2B}$, based on the affinity for $A_2$ receptor agonists, NECA and CGS-21680 (Mol. Pharmacol., Vol. 29, p. 331–346, (1986); J. Neurochem., Vol. 55, p. 1763–1771, (1990)). Four receptor subtypes, $A_1$, $A_2$ ($A_{2A}$ and $A_{2B}$) and $A_3$, have been identified until now. The $A_1$ receptor is a protein coupled receptor with a $G_{i/o}$ family of proteins. It serves to inhibit the adenylate cyclase as a result of binding with a ligand to thereby decrease the cAMP level and serves to activate phospholipase C (PLC) to thereby promote the production of inositol-1,4,5-triphosphate ($IP_3$) and to release the intracellular calcium ions. The $A_3$ receptor is a receptor serving to decrease the cAMP level and to activate PLC to thereby promote the $IP_3$ production and the release of calcium ions, as the $A_1$ receptor. In contrast, the $A_{2A}$ and $A_{2B}$ receptors are receptors serving to activate the adenylate cyclase and promote the production of cAMP. There is a report that the $A_{2B}$ receptor couples with PLC via a $G_q/G_{11}$ protein or promotes the production of $IP_3$ and the flow of calcium ions into cells (Clin. Invest. Vol. 96, p. 1979–1986 (1995)).

These subtypes are different from one another in their distribution in tissues; that is, the $A_1$ receptor occurs relatively abundantly, for example, in the heart, aorta and bladder, the $A_{2A}$ receptor is distributed relatively abundantly, for example, in the eyeballs and skeletal muscles, the $A_3$ receptor, for example, in the spleen, uterus, and prostate, and the $A_{2B}$ receptor, for example, in the proximal colon, and subsequently in the eyeballs, lung, uterus and bladder (Br. J. Pharmacol., Vol. 118, p. 1461–1468 (1996)). It is believed that these adenosine receptor subtypes can exhibit specific functions, respectively, due to the difference in distribution in the tissues as well as the difference in adenosine level among the locations and the difference in affinity for the ligand among the subtypes.

Adenosine is involved in a variety of physiological functions, such as platelet aggregation, heart rate, smooth muscle tonus, inflammation, release of neurotransmitters, neurotransmission, hormone release, cell-differentiation, cell growth, cell death, and DNA biosynthesis. Accordingly, the relation between adenosine and diseases, such as central nervous system diseases, cardiovascular diseases, inflammatory diseases, respiratory diseases, and immune diseases, has been suggested, and the efficacy of agonists/antagonists of the adenosine receptors on these diseases has been expected. Antagonists against the adenosine receptors, particularly those against the adenosine $A_2$ receptors have been discussed as effective as an agent for treating or preventing diabetes mellitus, diabetic complications, diabetic retinopathy, obesity or asthma and have been expected useful as, for example, a hypoglycemic agent, an agent for improving glucose intolerance, an insulin sensitizer, a hypotensive agent, a diuretic agent, an agent for treating osteoporosis, an agent for treating Parkinson's disease, an agent for treating Alzheimer's disease, an agent for treating an inflammatory bowel disease, or an agent for treating Crohn's disease.

Certain important reports have been made on the relation between the adenosine $A_2$ receptor and the intestinal tract. For example, certain reports have been made that the $A_2$ receptor mediates a colon longitudinal muscle relaxation action (Naunyn-Schmiedeberg's Arch. Pharmacol., 359, 140–146 (1999)), and that the $A_1$ receptor, and the $A_{2B}$ receptor occurring in the longitudinal muscle mediate a relaxation action of adenosine against the contraction of distal colon longitudinal muscle of a guinea pig (Br. J. Pharmacol., 129, 871–876 (2000)). Such $A_{2B}$ receptor antagonists do not induce diarrhea, have an excellent defecation-promoting action and are expected as an agent for treating and/or preventing various constipation. They are also expected as being useful for treating and/or preventing irritable bowel syndrome, constipation accompanying irritable bowel syndrome, organic constipation or constipation accompanying enteroparalytic ileus and for evacuating intestinal tracts at the time of examination of digestive tracts or before and after an operation.

For example, the following compounds (1)–(3) have been reported as having an antagonism against the $A_{2B}$ receptor.

(1) Compounds represented by the formulae:

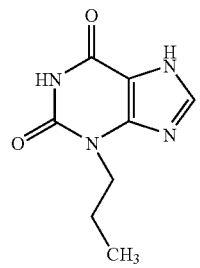

3-n-Propylxanthine

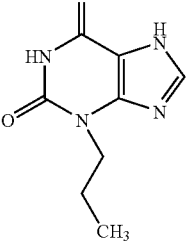

Theophylline

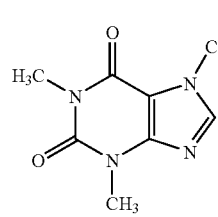
Caffeine

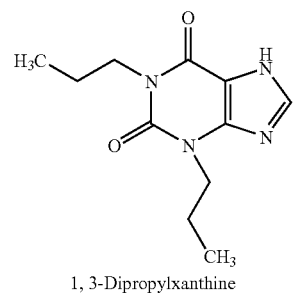
1, 3-Dipropylxanthine

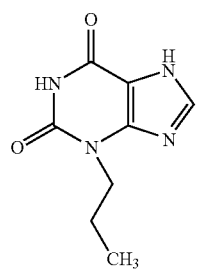
Enprofylline

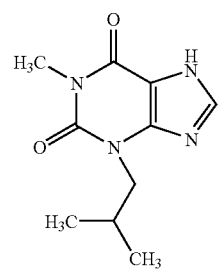
1-Methyl-3-isobutylxanthine

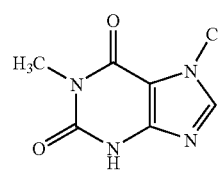
Paraxanthine

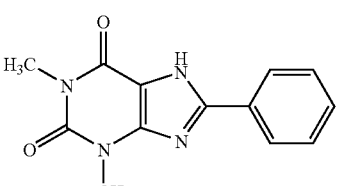
8-Phenyltheophylline

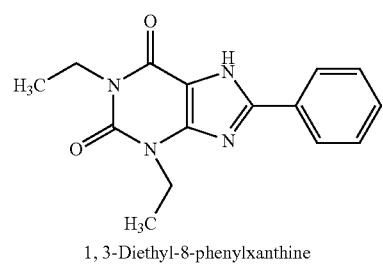
1, 3-Diethyl-8-phenylxanthine

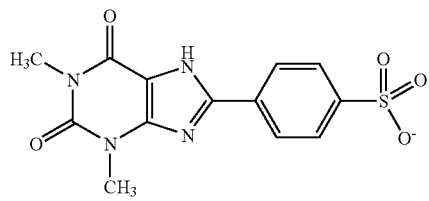
1, 3-Dimethyl-8-(p-sulfonyl) xanthine

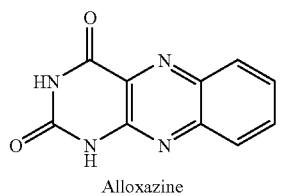
Alloxazine

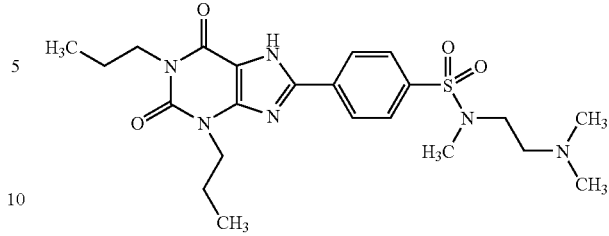
8-[4-[[[Methyl-(2-dimethylaminoethyl)-amino] sulfonylphenyl]-1, 3- Dipropylxanthine

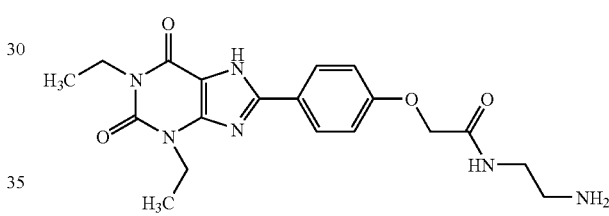
1, 3-Dipropyl-8-(p-sulfonyl) xanthine

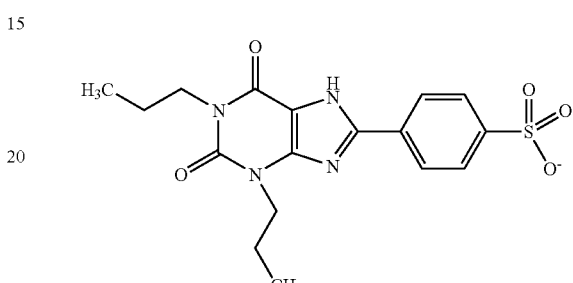
8-[4-[ [ [ [(2-Aminoethyl) amino] carbonyl] methyl] oxylphenl]-1, 3-dipropylxanthine

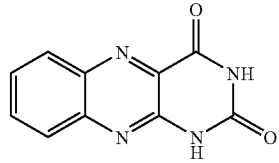
2, 4-Dioxobenzo [g] pteridine (2) A purine derivative represented by the formula:

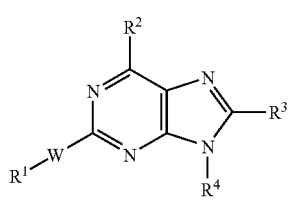

(wherein $R^1$ represents (1) the formula:

(wherein X represents a hydrogen atom, a hydroxyl group, a lower alkyl group which may be substituted, a lower alkoxy group which may be substituted, etc.; and $R^5$ and $R^6$ are the same as or different from each other and each represents a hydrogen atom, a lower alkyl group which may be substituted, a saturated or unsaturated cycloalkyl group having three to eight carbon atoms which may be substituted, etc.) or (2) a 5 or 6-membered aromatic ring which may have one or more substituents and a hetero atom; W represents the formula: —CH$_2$CH$_2$—, —CH═CH— or —C≡C—; $R^2$ represents an amino group which may be substituted with a lower alkyl group which may be substituted, etc.; $R^3$ represents a cycloalkyl group having three to eight carbon atoms which may be substituted, an aryl group which may be substituted, etc.; and $R^4$ represents a lower alkyl group which may be substituted, etc.), a pharmacologically acceptable salt thereof or a hydrate of them (JP-A 11-263789).

(3) A purine compound represented by the formula:

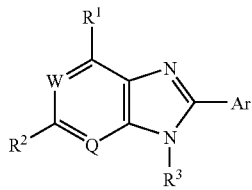

(wherein $R^1$ represents a hydrogen atom, a hydroxyl group, a halogen atom, an alkyl group having one to eight carbon atoms which may be substituted, etc.; $R^2$ represents an amino group which may be substituted with an alkyl group having one to eight carbon atoms, etc.; $R^3$ represents an alkynyl group having three to eight carbon atoms which may be substituted with a halogen atom, a hydroxyl group or an alkyl group having one to four carbon atoms, etc.; Ar represents an aryl group which may be substituted, a heteroaryl group which may be substituted, etc.; and Q and W are the same as or different from each other and each represents N or CH), a pharmacologically acceptable salt thereof or a hydrate of them (JP-A 11-188484).

(4) $A_{2B}$ receptor antagonists described in Drug Development Research, 48: 95–103 (1999) and J. Med. Chem., 43: 1165–1172 (2000).

In contrast, pyrimidone compounds have been only reported as compounds in, for example, WO 98/24780. However, the relation between these compounds and the adenosine receptors has been neither reported nor suggested and has not yet been known.

As is described above, compounds having an adenosine receptor antagonism, among them, compounds having an adenosine A$_2$ receptor antagonism, and particularly compounds having an A$_{2B}$ receptor antagonism are expected to exhibit an excellent action as a medicament, and strong demands have been made to provide such compounds. However, compounds which have an excellent antagonism against the adenosine receptors and effectively act as a medicament have not yet been found. Accordingly, an object of the present invention is to search for and find compounds which serve to inhibit the adenosine receptors (in particular A$_2$ receptor, A$_{2B}$ receptor) and are useful as an agent for treating or preventing a disease to which the adenosine receptors relate.

DISCLOSURE OF THE INVENTION

After intensive investigations under these circumstances, the present inventors have succeeded, for the first time, to synthesize a compound represented by the formula:

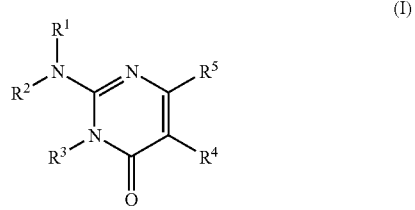

(I)

(in the formula, $R^1$ and $R^2$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic cyclic hydrocarbon group having six to fourteen carbon atoms which may be substituted, a 5 to 14-membered aromatic heterocyclic group which may be substituted, an acyl group having one to six carbon atoms which may be substituted or an alkylsulfonyl group having one to six carbon atoms which may be substituted; $R^3$ represents a hydrogen atom, an alkyl group having one to six carbon atoms which may be substituted, an alkenyl group having two to six carbon atoms which may be substituted or an alkynyl group having two to six carbon atoms which may be substituted; $R^4$ represents an aromatic cyclic hydrocarbon group having six to fourteen carbon atoms which may be substituted, a 5 to 14-membered aromatic heterocyclic group which may be substituted or a 5 to 14-membered non-aromatic heterocyclic group having at least one unsaturated bond which may be substituted; and $R^5$ represents an aromatic cyclic hydrocarbon group having six to fourteen carbon atoms which may be substituted or a 5 to 14-membered aromatic heterocyclic group which may be substituted), a salt thereof or a solvate of them. They have unexpectedly found that the compound and a salt thereof have an excellent antagonism against the adenosine A$_2$ receptors, particularly against the A$_{2B}$ receptor. After further intensive investigations, they have found that the compound, a salt thereof or a solvate of them has an efficacy on diseases to which the adenosine receptors, particularly the adenosine A$_2$ receptors, further particularly the adenosine A$_{2B}$ receptor relates, and that it is efficacious for preventing and/or treating various constipation (e.g., irritable bowel syndrome, constipation accompanying irritable bowel syndrome, organic constipation, constipation accompanying enteroparalytic ileus, constipation accompanying congenital digestive tract dysfunction, or constipation accompanying ileus) and is also useful as an agent for treating, preventing or improving, for example, diabetes mellitus, diabetic complications, diabetic retinopathy, obesity or asthma, and as a hypoglycemic agent, an agent for improving glucose intolerance, an insulin sensitizer, a hypotensive agent, a diuretic agent, an agent for treating osteoporosis, an agent for treating Parkinson's disease, an agent for treating Alzheimer's disease, an agent for treating an inflammatory bowel disease or an agent for treating Crohn's disease. The present invention has been accomplished based on these findings.

Specifically, the present invention relates to, for example, (1) a compound represented by the formula:

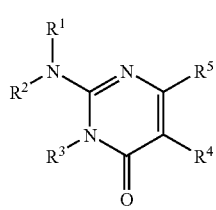

(I)

(in the formula, $R^1$ and $R^2$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic cyclic hydrocarbon group having six to fourteen carbon atoms which may be substituted, a 5 to 14-membered aromatic heterocyclic group which may be substituted, an acyl group having one to six carbon atoms which may be substituted or an alkylsulfonyl group having one to six carbon atoms which may be substituted; $R^3$ represents a hydrogen atom, an alkyl group having one to six carbon atoms which may be substituted, an alkenyl group having two to six carbon atoms which may be substituted or an alkynyl group having two to six carbon atoms which may be substituted; $R^4$ represents an aromatic cyclic hydrocarbon group having six to fourteen carbon atoms which may be substituted, a 5 to 14-membered aromatic heterocyclic group which may be substituted or a 5 to 14-membered non-aromatic heterocyclic group having at least one unsaturated bond which may be substituted; and $R^5$ represents an aromatic cyclic hydrocarbon group having six to fourteen carbon atoms which may be substituted or a 5 to 14-membered aromatic heterocyclic group which may be substituted), a salt thereof or a solvate of them; (2) the compound according to the above (1), a salt thereof or a solvate of them, wherein $R^4$ is 4-pyridyl group, 4-pyrimidinyl group, 4-quinazolinyl group, 4-quinolyl group, 6-isoquinolyl group, each of which may be substituted, or a 5 to 14-membered non-aromatic heterocyclic group having at least one of unsaturated bond which may be substituted; (3) the compound according to the above (1) or (2), a salt thereof or a solvate of them, wherein $R^4$ is represented by the formula:

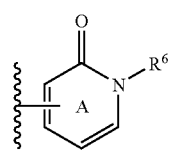

(II)

(wherein $R^6$ represents a group selected from the following Substituent Group a; and the ring A may be substituted with one to four groups selected from the following Substituent Group a: <Substituent Group a> the group consisting of a hydrogen atom, a halogen atom, a hydroxyl group, a nitro group, a cyano group, an alkyl group having one to six carbon atoms which may be substituted, an alkenyl group having two to six carbon atoms which may be substituted, an alkynyl group having two to six carbon atoms which may be substituted, an alkoxy group having one to six carbon atoms which may be substituted, an alkenyloxy group having two to six carbon atoms which may be substituted, an alkynyloxy group having two to six carbon atoms which may be substituted, an alkylthio group having one to six carbon atoms which may be substituted, an alkenylthio group having two to six carbon atoms which may be substituted, an alkynylthio group having two to six carbon atoms which may be substituted, an aliphatic acyl group having two to seven carbon atoms, a carbamoyl group which may be substituted, an arylacyl group, a heteroarylacyl group, an amino group which may be substituted, an alkylsulfonyl group having one to six carbon atoms which may be substituted, an alkenylsulfonyl group having two to six carbon atoms which may be substituted, an alkynylsulfonyl group having two to six carbon atoms which may be substituted, an alkylsulfinyl group having one to six carbon atoms which may be substituted, an alkenylsulfinyl group having two to six carbon atoms which may be substituted, an alkynylsulfinyl group having two to six carbon atoms which may be substituted, a formyl group, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic cyclic hydrocarbon group having six to fourteen carbon atoms which may be substituted and a 5 to 14-membered aromatic heterocyclic group which may be substituted); (4) the compound according to the above (3), a salt thereof or a solvate of them, wherein $R^4$ is represented by the formula:

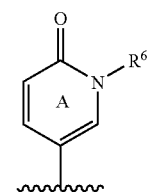

(III)

or the formula:

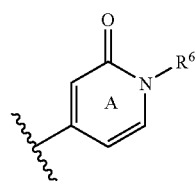

(IV)

(in the formulae (III) and (IV), $R^6$ represents a group selected from the above-mentioned Substituent Group a; and the ring A represents a nitrogen-containing 6-membered ring which may be substituted with one to four groups selected from the above mentioned Substituent Group a); (5) the compound according to the above (1) or (2), a salt thereof or a solvate of them, wherein R⁴ is 4-pyridyl group which may be substituted; (6) the compound according to any one of the above (1) to (5), a salt thereof or a solvate of them, wherein R¹ and/or R² is a hydrogen atom, an alkyl group having one to six carbon atoms which may be substituted, or an acyl group having one to six carbon atoms which may be substituted; (7) the compound according to any one of the above (1) to (6), a salt thereof or a solvate of them, wherein R⁵ is phenyl group, pyrrolyl group, pyridyl group, pyridazinyl group, pyrimidinyl group, pyrazinyl group, thienyl group, thiazolyl group, furyl group, naphthyl group, quinolinyl group, isoquinolinyl group, phthalazinyl group, naphthyridinyl group, indolyl group or isoindolyl group, each of which may be substituted; (8) a pharmaceutical composition comprising the compound according to any one of the above (1) to (7), a salt thereof or a solvate of them; (9) the composition according to the above (8), which is an agent for treating or preventing a disease to which an adenosine receptor relates; (10) the composition according to the above (8), which is an agent for treating or preventing a disease to which an adenosine $A_2$ receptor relates; (11) the composition according to the above (8), which is an agent for treating or preventing a disease to which an adenosine $A_{2B}$ receptor relates; (12) the composition according to the above (8), which is an adenosine receptor antagonist; (13) the composition according to the above (8), which is an adenosine $A_2$ receptor antagonist; (14) the composition according to the above (8), which is adenosine $A_{2B}$ receptor antagonist; (15) the composition according to the above (8), which is a defecation-promoting agent; (16) the composition according to the above (8), which is an agent for treating, preventing or improving constipation; (17) the composition according to the above (16), wherein the constipation is functional constipation; (18) the composition according to the above (8), which is an agent for treating, preventing or improving irritable bowel syndrome, constipation accompanying irritable bowel syndrome, organic constipation, constipation accompanying enteroparalytic ileus, constipation accompanying congenital digestive tract dysfunction or constipation accompanying ileus; (19) the composition according to the above (8), which is used for evacuating intestinal tracts at the time of examination of digestive tracts or before and after an operation; (20) use of the compound according to any one of the above (1) to (7), a salt thereof or a solvate of them for producing a defecation-promoting agent; (21) the composition according to the above (8), which is an agent for treating or preventing diabetes mellitus, diabetic complications, diabetic retinopathy, obesity or asthma; (22) the composition according to the above (8), which is a hypoglycemic agent, an agent for improving glucose intolerance or an insulin sensitizer; and (23) the composition according to the above (8), which is a hypotensive agent, a diuretic agent, an agent for treating osteoporosis, an agent for treating Parkinson's disease, an agent for treating Alzheimer's disease, an agent for treating an inflammatory bowel disease or an agent for treating Crohn's disease.

Hereinafter, the meanings of symbols, terms, etc. used in the present description will be described, and the present invention will be illustrated in detail.

In the present description, the "antagonist" refers to an agent which has affinity for and inactivates an adenosine receptor, preferably an adenosine $A_2$ receptor, and more preferably an $A_{2B}$ receptor.

The "disease to which an adenosine receptor relates" used in the present description refers to a disease to which an adenosine $A_1$ receptor, $A_{2A}$ receptor, $A_{2B}$ receptor or $A_3$ receptor relates, and includes various constipation (e.g., functional constipation, irritable bowel syndrome, constipation accompanying irritable bowel syndrome, organic constipation, constipation accompanying enteroparalytic ileus, constipation accompanying congenital digestive tract dysfunction and constipation accompanying ileus), diabetes mellitus, diabetic complications, diabetic retinopathy, obesity, asthma, as well as diseases against which a hypoglycemic agent, agent for improving glucose intolerance, insulin sensitizer, antihypertensive drug, diuretic agent, agent for treating osteoporosis, agent for treating Parkinson's disease, agent for treating Alzheimer's disease, agent for treating an inflammatory bowel disease or agent for treating Crohn's disease is efficacious.

The present invention provides a method for treating or preventing a disease to which an adenosine receptor relates, and a method for promoting defecation, which comprises administering a pharmacologically effective dose of the compound represented by the formula (I), a salt thereof or a solvate of them to a patient.

The present invention further provides use of the compound represented by the formula (I), a salt thereof or a solvate of them for producing an agent for treating or preventing a disease to which an adenosine receptor relates, or a defecation-promoting agent.

The compound represented by the formula (I), a salt thereof or a solvate of them is also useful as a defecation-promoting agent and is used for evacuating intestinal tracts at the time of examination of digestive tracts or before and after an operation.

The term "and/or" used in the present description means and includes both the cases of "and" and "or".

In the present description, there is the case where the structural formula of a compound represents a definite isomer for the sake of convenience. However, the present invention includes all isomers such as geometrical isomers, optical isomers based on asymmetric carbon, stereoisomers and tautomers, and mixtures of these isomers and is not limited by the description of the formula illustrated for the sake of convenience. The compound can be any of isomers or a mixture thereof. Accordingly, although it is possible that an asymmetric carbon atom is present in a molecule and that optically active substance and racemic substance may therefore be present, the present invention is not limited thereto but covers any of them. Further, crystal polymorphism may be present but, again, there is no limitation but any of single crystal form or a mixture will do. The compound (I) or its salt according to the present invention may be a non-solvate or a solvate, and either of them are included in the scope of claims for patent in the present invention. A metabolite which is generated by decomposing the compound (I) according to the present invention in vivo, and a prodrug of the compound (I) or its salt according to the present invention are also included in the scope of claims for patent in the present invention.

The "halogen atom" used in the present description represents an atom such as fluorine atom, chlorine atom, bromine atom or iodine atom, and fluorine atom, chlorine atom and bromine atom are preferred.

The "$C_{1-6}$ alkyl group" used in the present description represents an alkyl group having one to six carbon atoms, including linear or branched alkyl groups such as methyl group, ethyl group, n-propyl group, iso-propyl group, n-butyl group, iso-butyl group, sec-butyl group, t-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group, 1-methyl-2-ethylpropyl group, 1-ethyl-2-methylpropyl group, 1,1,2-trimethylpropyl group, 1-propylpropyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group or 3-methylpentyl group.

The "$C_{2-6}$ alkenyl group" used in the present description represents an alkenyl group having two to six carbon atoms, and suitable examples of the group are vinyl group, allyl group, 1-propenyl group, 2-propenyl group, isopropenyl group, 2-methyl-1-propenyl group, 3-methyl-1-propenyl group, 2-methyl-2-propenyl group, 3-methyl-2-propenyl group, 1-butenyl group, 2-butenyl group, 3-butenyl group, 1-pentenyl group, 1-hexenyl group, 1,3-hexadienyl group and 1,6-hexadienyl group.

The "$C_{2-6}$ alkynyl group" used in the present description represents an alkynyl group having two to six carbon atoms, and suitable examples of the group are ethynyl group, 1-propynyl group, 2-propynyl group, 1-butynyl group, 2-butynyl group, 3-butynyl group, 3-methyl-1-propynyl group, 1-ethynyl-2-propynyl group, 2-methyl-3-propynyl group, 1-pentynyl group, 1-hexynyl group, 1,3hexadiynyl group, and 1,6-hexadiynyl group.

The "$C_{1-6}$ alkoxy group" used in the present description represents an alkoxy group having one to six carbon atoms, such as methoxy group, ethoxy group, n-propoxy group, iso-propoxy group, sec-propoxy group, n-butoxy group, iso-butoxy group, sec-butoxy group, t-butoxy group, n-pentyloxy group, iso-pentyloxy group, sec-pentyloxy group, n-hexoxy group, iso-hexoxy group, 1,1-dimethylpropyloxy group, 1,2-dimethylpropoxy group, 2,2-dimethylpropyloxy group, 2-ethylpropoxy group, 1-methyl-2-ethylpropoxy group, 1-ethyl-2-methylpropoxy group, 1,1,2-trimethylpropoxy group, 1,1-dimethylbutoxy group, 1,2-dimethylbutoxy group, 2,2-dimethylbutoxy group, 2,3-dimethylbutyloxy group, 2-ethylbutoxy group, 1,3-dimethylbutoxy group, 2-methylpentoxy group, 3-methylpentoxy group or hexyloxy group.

The "$C_{2-6}$ alkenyloxy group" used in the present description represents an alkenyloxy group having two to six carbon atoms, and suitable examples of the group are vinyloxy group, allyloxy group, 1-propenyloxy group, 2-propenyloxy group, isopropenyloxy group, 2-methyl-1-propenyloxy group, 3-methyl-1-propenyloxy group, 2-methyl-2-propenyloxy group, 3-methyl-2-propenyloxy group, 1-butenyloxy group, 2-butenyloxy group, 3-butenyloxy group, 1-pentenyloxy group, 1-hexenyloxy group, 1,3-hexadienyloxy group, and 1,6-hexadienyloxy group.

The "$C_{2-6}$ alkynyloxy group" used in the present description represents an alkynyloxy group having two to six carbon atoms, and suitable examples thereof are ethynyloxy group, 1-propynyloxy group, 2-propynyloxy group, 1-butynyloxy group, 2-butynyloxy group, 3-butynyloxy group, 3-methyl-1-propynyloxy group, 1-ethynyl-2-propynyloxy group, 2-methyl-3-propynyloxy group, 1-pentynyloxy group, 1-hexynyloxy group, 1,3-hexadiynyloxy group, and 1,6-hexadiynyloxy group.

The "alkylthio group having one to six carbon atoms" used in the present description refers to an alkylthio group having one to six carbon atoms, such as methylthio group, ethylthio group, n-propylthio group, iso-propylthio group, sec-propylthio group, n-butylthio group, iso-butylthio group, sec-butylthio group, t-butylthio group, n-pentylthio group, iso-pentylthio group, sec-pentylthio group, n-hexylthio group, iso-hexylthio group, 1,1-dimethylpropylthio group, 1,2-dimethylpropylthio group, 2,2-dimethylpropylthio group, 2-ethylpropylthio group, 1-methyl-2-ethylpropylthio group, 1-ethyl-2-methylpropylthio group, 1,1,2-trimethylpropylthio group, 1,1-dimethylbutylthio group, 1,2-dimethylbutylthio group, 2,2-dimethylbutylthio group, 2,3-dimethylbutylthio group, 1,3-dimethylbutylthio group, 2-ethylbutylthio group, 2-methylpentylthio group or 3-methylpentylthio group.

The "alkenylthio group having two to six carbon atoms" used in the present description refers to an alkenylthio group having two to six carbon atoms, and suitable examples thereof are vinylthio group, allylthio group, 1-propenylthio group, 2-propenylthio group, isopropenylthio group, 2-methyl-1-propenylthio group, 3-methyl-1-propenylthio group, 2-methyl-2-propenylthio group, 3-methyl-2-propenylthio group, 1-butenylthio group, 2-butenylthio group, 3-butenylthio group, 1-pentenylthio group, 1-hexenylthio group, 1,3-hexadienylthio group, and 1,6-hexadienylthio group.

The "alkynylthio group having two to six carbon atoms" used in the present description represents an alkynylthio group having two to six carbon atoms, and suitable examples thereof are ethynylthio group, 1-propynylthio group, 2-propynylthio group, 1-butynylthio group, 2-butynylthio group, 3-butynylthio group, 3-methyl-1-propynylthio group, 1-ethynyl-2-propynylthio group, 2-methyl-3-propynylthio group, 1-pentynylthio group, 1-hexynylthio group, 1,3-hexadiynylthio group, and 1,6-hexadiynylthio group.

The "cycloalkyl group having three to eight carbon atoms" used in the present description represents a cycloalkyl group comprising three to eight carbon atoms, such as cyclopropyl group, cyclobutyl group, cyclopentyl group, cyclohexyl group, cycloheptyl group or cyclooctyl group.

The "cycloalkenyl group having three to eight carbon atoms" used in the present invention represents a cycloalkenyl group comprising three to eight carbon atoms, such as cyclopropen-1-yl, cyclopropen-3-yl, cyclobuten-1-yl, cyclobuten-3-yl, 1,3-cyclobutadien-1-yl, cyclopenten-1-yl, cyclopenten-3-yl, cyclopenten-4-yl, 1,3-cyclopentadien-1-yl, 1,3-cyclopentadien-2-yl, 1,3-cyclopentadien-5-yl, cyclohexen-1-yl, cyclohexen-3-yl, cyclohexen-4-yl, 1,3-cyclohexadien-1-yl, 1,3-cyclohexadien-2-yl, 1,3-cyclohexadien-5-yl, 1,4-cyclohexadien-3-yl, 1,4-cyclohexadien-1-yl, cyclohepten-1-yl, cyclohepten-3-yl, cyclohepten-4-yl, cyclohepten-5-yl, 1,3-cyclohepten-2-yl, 1,3-cyclohepten-1-yl, 1,3-cycloheptadien-5-yl, 1,3-cycloheptadien-6-yl, 1,4-cycloheptadien-3-yl, 1,4-cycloheptadien-2-yl, 1,4-cycloheptadien-1-yl, 1,4-cycloheptadien-6-yl, 1,3,5-cycloheptatrien-3-yl, 1,3,5-cycloheptatrien-2-yl, 1,3,5-cycloheptatrien-1-yl, 1,3,5-cycloheptatrien-7-yl, cycloocten-1-yl, cycloocten-3-yl, cycloocten-4-yl, cycloocten-5-yl, 1,3-cyclooctadien-2-yl, 1,3-cyclooctadien-1-yl, 1,3-cyclooctadien-5-yl, 1,3-cyclooctadien-6-yl, 1,4-cyclooctadien-3-yl, 1,4-cyclooctadien-2-yl, 1,4-cyclooctadien-1-yl, 1,4-cyclooctadien-6-yl, 1,4-cyclooctadien-7-yl, 1,5-cyclooctadien-3-yl, 1,5-cyclooctadien-2-yl, 1,3,5-cyclooctatrien-3-yl, 1,3,5-cyclooctatrien-2-yl, 1,3,5-cyclooctatrien-1-yl, 1,3,5-cyclooctatrien-7-yl, 1,3,6-cyclooctatrien-2-yl, 1,3,6-cyclooctatrien-1-yl, 1,3,6-cyclooctatrien-5-yl or 1,3,6-cyclooctatrien-6-yl group.

The "5 to 14-membered non-aromatic heterocyclic group" used in the present description refers to a monocyclic, bicyclic or tricyclic 5 to 14-membered non-aromatic heterocyclic group and containing one or more hetero atoms selected from the group consisting of nitrogen atom, sulfur atom and oxygen atom. Specific examples of the group are pyrrolidinyl group, piperidinyl group, piperazinyl group, pyrazolinyl group, morpholinyl group, tetrahydrofuryl group, tetrahydropyranyl group, dihydrofuryl group, dihydropyranyl group, imidazolinyl group, and oxazolinyl group. The non-aromatic heterocyclic group also includes a group derived from pyridone ring, and a non-aromatic fused ring (e.g., a group derived from phthalimide ring or succinimide ring).

The "aromatic cyclic hydrocarbon group having six to fourteen carbon atoms" and the "aryl" used in the present description represent an aromatic cyclic hydrocarbon group comprising six to fourteen carbon atoms and include monocyclic groups, as well as fused groups such as bicyclic groups and tricyclic groups. Specific examples of the group include phenyl group, indenyl group, 1-naphthyl group, 2-naphthyl group, azulenyl group, heptalenyl group, biphenyl group, indacenyl group, acenaphthyl group, fluorenyl group, phenalenyl group, phenanthrenyl group, anthracenyl group, cyclopentacyclooctenyl group, and benzocyclooctenyl group.

The "5 to 14-membered aromatic heterocyclic group" and the "heteroaryl" used in the present description represent a monocyclic, bicyclic or tricyclic 5 to 14-membered aromatic heterocyclic group containing one or more hetero atoms selected from nitrogen atom, sulfur atom and oxygen atom. Specific examples of the group include 1) a nitrogen-containing aromatic heterocyclic group such as pyrrolyl group, pyridyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, quinolyl group, isoquinolyl group, quinolizyl group, phthalazyl group, naphthyridinyl group, quinoxalyl group, quinazolinyl group, cinnolinyl group, pteridinyl group, imidazotriazinyl group, pyrazinopyridazinyl group, acridinyl group, phenanthridinyl group, carbazolyl group, carbazolinyl group, perimidinyl group, phenanthrolinyl group, phenacinyl group, imidazopyridinyl group, imidazopyrimidinyl group, pyrazolopyridinyl group or pyrazolopyridinyl group; 2) a sulfur-containing aromatic heterocyclic group such as thienyl group or benzothienyl group; 3) an oxygen-containing aromatic heterocyclic group such as furyl group, pyranyl group, cyclopentapyranyl group, benzofuryl group or isobenzofuryl group; and 4) an aromatic heterocyclic group containing two or more different hetero atoms, such as thiazolyl group, isothiazolyl group, benzothiazolyl group, benzthiadiazolyl group, phenothiazinyl group, isoxazolyl group, furazanyl group, phenoxazinyl group, oxazolyl group, isoxazolyl group, benzoxazolyl group, oxadiazolyl group, pyrazolooxazolyl group, imidazothiazolyl group, thienofuranyl group, furopyrrolyl group or pyridooxazinyl group.

The "aliphatic acyl group having two to seven carbon atoms" used in the present description represents an atomic group derived from an aliphatic carboxyl group having two to seven carbon atoms by removing OH group from its carboxyl group, and suitable examples thereof are acetyl group, propionyl group and butyroyl group.

The "arylacyl group" used in the present description represents a carbonyl group substituted with an aromatic cyclic hydrocarbon group having six to fourteen carbon atoms, and the "heteroarylacyl group" represents a carbonyl group substituted with a 5 to 14-membered aromatic heterocyclic group. The "aromatic cyclic hydrocarbon group having six to fourteen carbon atoms" and the "5 to 14-membered aromatic heterocyclic group" as used herein have the same meanings as defined above.

Suitable examples of the "alkylsulfonyl group having one to six carbon atoms", "alkenylsulfonyl group having two to six carbon atoms" and "alkynylsulfonyl group having two to six carbon atoms" used in the present description include methylsulfonyl group, ethylsulfonyl group, n-propylsulfonyl group, iso-propylsulfonyl group, n-butylsulfonyl group, t-butylsulfonyl group, vinylsulfonyl group, allylsulfonyl group, iso-propenylsulfonyl group, iso-pentenylsulfonyl group, and ethynylsulfonyl group. Suitable examples of the "alkylsulfinyl group having one to six carbon atoms", "alkenylsulfinyl group having two to six carbon atoms" and "alkynylsulfinyl group having two to six carbon atoms" used in the present description include methylsulfinyl group, ethylsulfinyl group, n-propylsulfinyl group, iso-propylsulfinyl group, n-butylsulfinyl group, t-butylsulfinyl group, vinylsulfinyl group, allylsulfinyl group, iso-propenylsulfinyl group, iso-pentenylsulfinyl group, and ethynylsulfinyl group.

Examples of the "substituents" in the "amino group which may be substituted" used in the present description represents one or two groups selected from an alkyl group having one to six carbon atoms, an alkenyl group having two to six carbon atoms, an alkynyl group having two to six carbon atoms, an alkylsulfonyl group having one to six carbon atoms, an alkenylsulfonyl group having two to six carbon atoms, alkynylsulfonyl group having two to six carbon atoms, an alkylcarbonyl group having one to six carbon atoms, an alkenylcarbonyl group having two to six carbon atoms, an alkynylcarbonyl group having two to six carbon atoms, each of which may be substituted. In this connection, the substituents may be combined to form a 3 to 8-membered nitrogen-containing ring. Suitable examples of the "substituents" in the alkyl group having one to six carbon atoms, alkenyl group having two to six carbon atoms, alkynyl group having two to six carbon atoms, alkylsulfonyl group having one to six carbon atoms, alkenylsulfonyl group having two to six carbon atoms, alkynylsulfonyl group having two to six carbon atoms, $C_{1-6}$ alkyl-carbonyl group, $C_{2-6}$ alkenyl-carbonyl group and $C_{2-6}$ alkynyl-carbonyl group include a hydroxyl group, a halogen atom, a nitrile group, an alkoxy group has iso-pentylamino group, neopentylamino group, n-hexylamino group, 1-methylpropylamino group, 1,2-dimethylpropylamino group, 2-ethylpropylamino group, 1-methyl-2-ethylpropylamino group, 1-ethyl-2-methylpropylamino group, 1,1,2-trimethylpropylamino group, 1-methylbutylamino group, 2-methylbutylamino group, 1,1-dimethylbutylamino group, 2,2-dimethylbutylamino group, 2-ethylbutylamino group, 1,3-dimethylbutylamino group, 2-methylpentylamino group, 3-methylpentylamino group, N,N-dimethylamino group, N,N-diethylamino group, N,N-di(n-propyl)amino group, N,N-di(iso-propyl)amino group, N,N-di(n-butyl)amino group, N,N-di(iso-butyl)amino group, N,N-di(t-butyl)amino group, N,N-di(n-pentyl)amino group, N,N-di(iso-pentyl)amino group, N,N-di(neopentyl) amino group, N,N-di(n-hexyl)amino group, N,N-di(1-methylpropyl)amino group, N,N-di (1,2-dimethylpropyl)amino group, N-methyl-N-ethylamino group, N-ethyl-N-(n-propyl)amino group, N-methyl-N-(i-propyl)amino group, vinylamino group, allylamino group, (1-propenyl)amino group, isopropenylamino group, (1-buten-1-yl)amino group, (1-buten-2-yl)amino group, (1-buten-3-yl)amino group, (2-buten-1-yl)amino group, (2-buten-2-yl)amino group, N,N-divinylamino group, N,N-diallylamino group, N,N-di (1-propenyl)amino group, N,N-isopropenylamino group, N-vinyl-N-allylamino group, ethynylamino group, 1-propynylamino group, 2-propynylamino group, butynylamino group, pentynylamino group, hexynylamino group, N,N-diethynylamino group, N,N-(1-propynyl)amino group, N,N-(2-propynyl)amino group, N,N-dibutynylamino group, N,N-dipentynylamino group, N,N-dihexynylamino group, hydroxymethylamino group, 1-hydroxyethylamino group, 2-hydroxyethylamino group, 3-hydroxy-n-propyl group, methylsulfonylamino group, ethylsulfonylamino group, n-propylsulfonylamino group, iso-propylsulfonylamino group, n-butylsulfonylamino group, t-butylsulfonylamino group, vinylsulfonylamino group, allylsulfonylamino group, iso-propenylsulfonylamino group, iso-pentenylsulfonylamino group, ethynylsulfonylamino group, methylcarbonylamino group, ethylcarbonylamino group, n-propylcarbonylamino group, iso-propylcarbonylamino group, n-butylcarbonylamino group, t-butylcarbonylamino group, vinylcarbonylamino group, allylcarbonylamino group, iso-propenylcarbonylamino group, iso-pentenylcarbonylamino group, and ethynylcarbonylamino group.

Examples of the "substituents" in the phrase "which may be substituted" used in the present description include a halogen atom such as fluorine atom, chlorine atom, bromine atom or iodine atom; a hydroxyl group; a nitro group; a cyano group; an alkyl group having one to six carbon atoms such as methyl group, ethyl group, n-propyl group, iso-propyl group, n-butyl group, iso-butyl group, sec-butyl group, t-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group or 1-methyl-2-ethylpropyl group; an alkenyl group having two to six carbon atoms such as vinyl group, allyl group, 1-propenyl group, 2-propenyl group, isopropenyl group, 2-methyl-1-propenyl group, 3-methyl-1-propenyl group, 2-methyl-2-propenyl group, 3-methyl-2-propenyl group, 1-butenyl group, 2-butenyl group, 3-butenyl group, 1-pentenyl group, 1-hexenyl group, 1,3-hexadienyl group or 1,6-hexadienyl group; an alkynyl group having two to six carbon atoms such as ethynyl group, 1-propynyl group, 2-propynyl group, 1-butynyl group, 2-butynyl group, 3-butynyl group, 3-methyl-1-propynyl group, 1-ethynyl-2-propynyl group, 2-methyl-3-propynyl group, 1-pentynyl group, 1-hexynyl group, 1,3-hexadiynyl group or 1,6-hexadiynyl group; an alkoxy group having one to six carbon atoms such as methoxy group, ethoxy group, n-propoxy group, iso-propoxy group, sec-propoxy group, n-butoxy group, iso-butoxy group, sec-butoxy group, t-butoxy group, n-pentyloxy group, iso-pentyloxy group, sec-pentyloxy group or n-hexyloxy group; an alkenyloxy group having two to six carbon atoms such as vinyloxy group, allyloxy group, 1-propenyloxy group, 2-propenyloxy group or isopropenyloxy group; an alkynyloxy group having two to six carbon atoms such as ethynyloxy group, 1-propynyloxy group or 2-propynyloxy group; an alkylthio group having one to six carbon atoms such as methylthio group, ethylthio group, n-propylthio group, iso-propylthio group, sec-propylthio group, n-butylthio group, iso-butylthio group, sec-butylthio group or t-butylthio group; an alkenylthio group having two to six carbon atoms such as vinylthio group, allylthio group, 1-propenylthio group or 2-propenylthio group; an alkynylthio group having two to six carbon atoms such as ethynylthio group, 1-propynylthio group or 2-propynylthio group; an aliphatic acyl group having two to seven carbon atoms such as acetyl group, propionyl group or butyroyl group; carbamoyl group; an arylacyl group; a heteroarylacyl group; an amino group; an alkylsulfonyl group having one to six carbon atoms, an alkenylsulfonyl group having two to six carbon atoms, an alkynylsulfonyl group having two to six carbon atoms, an alkylsulfinyl group having one to six carbon atoms, an alkenylsulfinyl group having two to six carbon atoms or an alkynylsulfinyl group having two to six carbon atoms, such as methylsulfonyl group, ethylsulfonyl group, n-propylsulfonyl group, iso-propylsulfonyl group, n-butylsulfonyl group, t-butylsulfonyl group, vinylsulfonyl group, allylsulfonyl group, iso-propenylsulfonyl group, iso-pentenylsulfonyl group, ethynylsulfonyl group, methylsulfinyl group, ethylsulfinyl group, n-propylsulfinyl group, iso-propylsulfinyl group, n-butylsulfinyl group, t-butylsulfinyl group, vinylsulfinyl group, allylsulfinyl group, iso-propenylsulfinyl group, iso-pentenylsulfinyl group or ethynylsulfinyl group; a formyl group, a cycloalkyl group having three to eight carbon atoms such as cyclopropyl group, cyclobutyl group, cyclopentyl group, cyclohexyl group, cycloheptyl group or cyclooctyl group; a cycloalkenyl group having three to eight carbon atoms such as cyclopropenyl, cyclobutenyl, cyclopentenyl or cyclohexenyl group; a 5 to 14-membered non-aromatic heterocyclic group, such as pyrrolidinyl group, pyrrolyl group, piperidinyl group, piperazinyl group, imidazolyl group, pyrazolidyl group, imidazolidyl group, morpholinyl group, tetrahydrofuryl group, tetrahydropyranyl group, pyrrolinyl group, dihydrofuryl group, dihydropyranyl group, imidazolinyl group, oxazolinyl group, a group derived from pyridone ring, and a group derived from phthalimide ring or succinimide ring; an aromatic cyclic hydrocarbon group having six to fourteen carbon atoms such as phenyl group, indenyl group, 1-naphthyl group, 2-naphthyl group, biphenyl group or indacenyl group; a 5 to 14-membered aromatic heterocyclic group, such as pyrrolyl group, pyridyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, quinolyl group, isoquinolyl group, quinolizinyl group, phthalazinyl group, naphthyridinyl group, quinoxalyl group, quinazolinyl group, cinnolinyl group, pteridinyl group, imidazotriazinyl group, pyrazinopyridazinyl group, acridinyl group, phenanthridinyl group, carbazolyl group, carbazolinyl group, perimidinyl group, phenanthrolinyl group, phenazinyl group, imidazopyridyl group, imidazopyrimidinyl group, pyrazolopyridyl group, pyrazolopyridyl group, thienyl group, benzothienyl group, furyl group, pyranyl group, cyclopentapyranyl group, benzofuryl group, isobenzofuryl group, thiazolyl group, isothiazolyl group, benzothiazolyl group, benzothiadiazolyl group, phenothiazinyl group, isoxazolyl group, furazanyl group, phenoxazinyl group, oxazolyl group, isoxazolyl group, benzoxazolyl group, oxadiazolyl group, pyrazolooxazolyl group, imidazothiazolyl group, thienofuranyl group, furopyrrolyl group or pyridooxazinyl group. Each of these substituents may be further substituted.

In the formula (I), suitable examples of the "substituents" in the "carbamoyl group which may be substituted" are groups selected from an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, an aromatic cyclic hydrocarbon group having six to fourteen carbon atoms which may be substituted, and a 5 to 14-membered aromatic heterocyclic group which may be substituted. The nitrogen atom of the carbamoyl group may be substituted with one or two groups selected from the above group of substituents. The substituents may be combined to form a 3 to 14-membered nitrogen-containing ring, such as pyrrolidyl group, pyrrolinyl group, piperidyl group, piperazinyl group, imidazolyl group, pyrazolidyl group, imidazolidyl group, morpholinyl group, tetrahydropyranyl group, aziridinyl group, oxiranyl group, oxathiolanyl group, phthalimidyl group, succinimidyl group, pyrrolyl group, pyridyl group, pyridazinyl group, pyrimidinyl group, pyrazinyl group or pyrazolyl group. In addition, the nitrogen-containing ring may be substituted.

In the formula (I), a preferred group in $R^1$ and/or $R^2$ is not specifically limited, of which a hydrogen atom, an alkyl group having one to six carbon atoms and an aliphatic acyl group having two to seven carbon atoms, each of which may be substituted, are more preferred, and a hydrogen atom is typically preferred.

In the formula (I), a preferred group in $R^3$ is not specifically limited, of which a hydrogen atom, an alkyl group having one to six carbon atoms, an alkenyl group having two to six carbon atoms or an alkynyl group having two to six carbon atoms, each of which may be substituted, is more preferred, and a hydrogen atom, methyl group, ethyl group, n-propyl group or allyl group is typically preferred.

In the formula (I), $R^4$ represents an aromatic cyclic hydrocarbon group having six to fourteen carbon atoms which may be substituted, a 5 to 14-membered non-aromatic heterocyclic group having one or more unsaturated bonds or a 5 to 14-membered aromatic heterocyclic group which may be substituted, and suitable examples thereof are an aromatic cyclic hydrocarbon group having six to fourteen carbon atoms such as phenyl group or naphthyl group; a 5 to 14-membered non-aromatic heterocyclic group, such as pyrrolidinyl group, pyrrolinyl group, piperidinyl group, piperazinyl group, imidazolinyl group, pyrazolidinyl group, imidazolidinyl group, morpholinyl group, tetrahydropyranyl group, aziridinyl group, oxiranyl group, oxathiolanyl group, 2-oxo-1,2-dihydropyridinyl group or 6-oxo-1,6-dihydropyridyl group which may be substituted on its nitrogen atom; or a 5 to 14-membered aromatic heterocyclic group, such as pyrrolyl group, pyridyl group, pyridazinyl group, pyrimidinyl group, pyrazinyl group, pyrazolyl group, imidazolyl group, indolyl group, isoindolyl group, indolizinyl group, quinolyl group, isoquinolyl group, quinolizinyl group, phthalazinyl group, naphthyridyl group, quinoxalyl group, quinazolyl group, imidazotriazinyl group, pyrazinopyridazinyl group, thienyl group, benzothienyl group, furyl group, pyranyl group, cyclopentapyranyl group, benzofuryl group, isobenzofuryl group, thiazolyl group, isothiazolyl group, benzothiazolyl group, benzothiadiazolyl group, phenothiazyl group, isoxazolyl group, pyrazolooxazolyl group, imidazothiazolyl group, thienofuryl group, furopyrrolyl group or pyridooxazinyl group. Each of these groups may be further substituted. More preferred examples of $R^4$ include groups represented by the formulae:

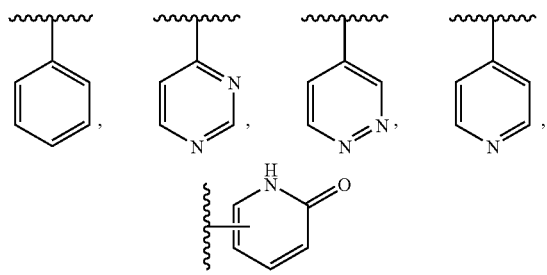

each of which may be substituted. When the 6-oxo-1,6-dihydropyridyl group or 2-oxo-1,2-dihydropyridyl group has a substituent, the substituent may also be combined with the nitrogen atom.

In the formula (I), $R^5$ refers to an aromatic cyclic hydrocarbon group having six to fourteen carbon atoms or a 5 to 14-membered aromatic heterocyclic group, each of which may be substituted, and suitable examples thereof include an aromatic cyclic hydrocarbon group having six to fourteen carbon atoms such as phenyl group or naphthyl group, or a 5 to 14-membered aromatic heterocyclic group, such as pyrrolyl group, pyridyl group, pyridazinyl group, pyrimidinyl group, pyrazinyl group, pyrazolyl group, imidazolyl group, indolyl group, isoindolyl group, indolizinyl group, quinolyl group, isoquinolyl group, quinolizinyl group, phthalazinyl group, naphthyridyl group, quinoxalyl group, quinazolyl group, imidazotriazinyl group, pyrazinopyridazinyl group, thienyl group, benzothienyl group, furyl group, pyranyl group, cyclopentapyranyl group, benzofuryl group, isobenzofuryl group, thiazolyl group, isothiazolyl group, benzothiazolyl group, benzothiadiazolyl group, phenothiazyl group, isoxazolyl group, pyrazolooxazolyl group, imidazothiazolyl group, thienofuryl group, furopyrrolyl group or pyridooxazinyl group. Each of these groups may be substituted. More preferred examples of $R^5$ include groups represented by the formulae:

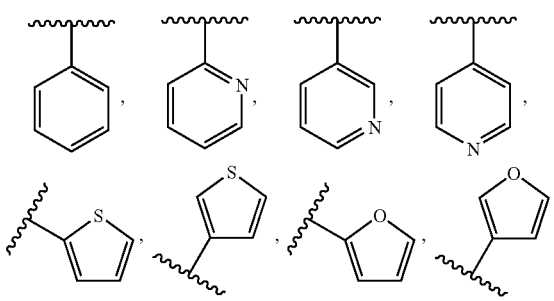

each of which may be substituted.

In the "substituents" in the "aromatic cyclic hydrocarbon group having six to fourteen carbon atoms which may be substituted" and the "5 to 14-membered aromatic heterocyclic group which may be substituted", (1) preferred examples are one or more groups selected from a hydroxyl group, a halogen atom, a cyano group, a nitro group, an alkyl group having one to six carbon atoms which may be substituted, an alkenyl group having two to six carbon atoms which may be substituted, an alkynyl group having two to six carbon atoms which may be substituted, an alkoxy group having one to six carbon atoms which may be substituted, an alkenyloxy group having two to six carbon atoms which may be substituted, an alkylthio group having one to six carbon atoms which may be substituted, an alkenylthio group having two to six carbon atoms which may be substituted, an alkynylthio group having two to six carbon atoms which may be substituted, a substituted carbonyl group, an amino group which may be substituted, an alkylsulfonyl group having one to six carbon atoms which may be substituted, an alkenylsulfonyl group having two to six carbon atoms which may be substituted, an alkynylsulfonyl group having two to six carbon atoms which may be substituted, an alkylsulfinyl group having one to six carbon atoms which may be substituted, an alkenylsulfinyl group having two to six carbon atoms which may be substituted, an alkynylsulfinyl group having two to six carbon atoms which may be substituted, a formyl group, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic cyclic hydrocarbon group having six to fourteen carbon atoms which may be substituted and a 5 to 14-membered aromatic heterocyclic group which may be substituted; (2) more preferably, one or more groups selected from (1) a hydroxyl group, (2) a halogen atom, (3) a cyano group, (4) a nitro group, (5) an alkyl group having one to six carbon atoms, an alkenyl group having two to six carbon atoms or an alkynyl group having two to six carbon atoms, each of which may be substituted with one or more groups selected from (i) a hydroxyl group, (ii) a cyano group, (iii) a halogen atom, (iv) an alkylamino group having one to six carbon atoms, (v) a di($C_{1-6}$ alkyl)amino group, (vi) a $C_{2-6}$ alkenylamino group, (vii) a di($C_{2-6}$ alkenyl)amino group, (viii) an alkynylamino group having two to six carbon atoms, (ix) a di($C_{2-6}$ alkynyl)amino group, (x) an N—$C_{1-6}$ alkyl-N—$C_{2-6}$ alkenylamino group, (xi) an N—$C_{1-6}$ alkyl-N—$C_{2-6}$ alkynylamino group, (xii) an N—$C_{2-6}$ alkenyl-N—$C_{2-6}$ alkynylamino group, (xiii) an aralkyloxy group, (xiv) a t-butyldimethylsilyloxy (TBDMS-oxy) group, (xv) a $C_{1-6}$ alkylsulfonylamino group, (xvi) a $C_{1-6}$ alkylcarbonyloxy group, (xvii) a $C_{2-6}$ alkenylcarbonyloxy group, (xviii) a $C_{2-6}$ alkynylcarbonyloxy group, (xix) an N—$C_{1-6}$ alkylcarbamoyl group, (xx) an N—$C_{2-6}$ alkenylcarbamoyl group and (xxi) an N—$C_{1-6}$ alkynylcarbamoyl group, (6) an alkoxy group having one to six carbon atoms, an alkenyloxy group having two to six carbon atoms or an alkynyloxy group having two to six carbon atoms, each of which may be substituted with one or more groups selected from (i) an alkylamino group having one to six carbon atoms, (ii) an aralkyloxy group and (iii) a hydroxyl group, (7) an alkylthio group having one to six carbon atoms, an alkenylthio group having two to six carbon atoms or an alkynylthio group having two to six carbon atoms, each of which may be substituted with one or more groups selected from (i) a hydroxyl group, (ii) a nitrile group, (iii) a halogen atom, (iv) an alkylamino group having one to six carbon atoms, (v) an aralkyloxy group, (vi) a TBDMS-oxy group, (vii) a $C_{1-6}$ alkylsulfonylamino group, (viii) a $C_{1-6}$ alkylcarbonyloxy group and (ix) a $C_{1-6}$ alkylcarbamoyl group, (8) carbonyl group substituted with a group selected from (i) an alkoxy group having one to six carbon atoms, (ii) an amino group, (iii) an alkylamino group having one to six carbon atoms, (iv) a di($C_{1-6}$ alkyl)amino group, (v) an alkenylamino group having two to six carbon atoms, (vi) a di($C_{2-6}$ alkenyl)amino group, (vii) an alkynylamino group having two to six carbon atoms, (vii) a di($C_{2-6}$ alkynyl)amino group, (viii) an N—$C_{1-6}$ alkyl-N—$C_{2-6}$ alkenylamino group, (ix) an N—$C_{1-6}$ alkyl-N—$C_{2-6}$ alkynylamino group and (x) an N—$C_{2-6}$ alkenyl-N—$C_{2-6}$ alkynylamino group, (9) an amino group which may be substituted with one or two groups selected from (i) an alkyl group having one to six carbon atoms, (ii) an alkenyl group having two to six carbon atoms, (iii) an alkynyl group having two to six carbon atoms, (iv) an alkylsulfonyl group having one to six carbon atoms, (v) an alkenylsulfonyl group having two to six carbon atoms, (vi) an alkynylsulfonyl group having two to six carbon atoms, (vii) a $C_{1-6}$ alkylcarbonyl group, (viii) a $C_{2-6}$ alkenylcarbonyl group and (ix) a $C_{2-6}$ alkynylcarbonyl group, (10) an alkylsulfonyl group having one to six carbon atoms, (11) an alkenylsulfonyl group having two to six carbon atoms, (12) an alkynylsulfonyl group having two to six carbon atoms, (13) an alkylsulfinyl group having one to six carbon atoms, (14) an alkenylsulfinyl group having two to six carbon atoms, (15) an alkynylsulfinyl group having two to six carbon atoms, (16) a formyl group, (17) a cycloalkyl group having three to eight carbon atoms or cycloalkenyl group having three to eight carbon atoms, each of which may be substituted with one or more groups selected from (i) a hydroxyl group, (ii) a halogen atom, (iii) a nitrile group, (iv) an alkyl group having one to six carbon atoms, (v) an alkoxy group having one to six carbon atoms, (vi) a $C_{1-6}$ alkoxy-$C_{1-6}$ alkyl group and (vii) an aralkyl group, (18) a 5 to 14-membered non-aromatic heterocyclic group which may be substituted with one or more groups selected from (i) a hydroxyl group, (ii) a halogen atom, (iii) a nitrile group, (iv) an alkyl group having one to six carbon atoms, (v) an alkoxy group having one to six carbon atoms, (vi) a $C_{1-6}$ alkoxy-$C_{1-6}$ alkyl group and (vii) an aralkyl group, (19) an aromatic cyclic hydrocarbon group having six to fourteen carbon atoms which may be substituted with one or more groups selected from (i) a hydroxyl group, (ii) a halogen atom, (iii) a nitrile group, (iv) an alkyl group having one to six carbon atoms, (v) an alkoxy group having one to six carbon atoms, (vi) a $C_{1-6}$ alkoxy-$C_{1-6}$ alkyl group and (vii) an aralkyl group, and (20) a 5 to 14-membered aromatic heterocyclic group which may be substituted with one or more groups selected from (i) a hydroxyl group, (ii) a halogen atom, (iii) a nitrile group, (iv) an alkyl group having one to six carbon atoms, (v) an alkoxy group having one to six carbon atoms, (vi) a $C_{1-6}$ alkoxy-$C_{1-6}$ alkyl group and (vii) an aralkyl group; and (3) most preferably, one or more groups selected from a hydroxyl group, a halogen atom (e.g., fluorine atom, chlorine atom bromine atom or iodine atom), a cyano group, a nitro group, an alkyl group having one to six carbon atoms (e.g., methyl group, ethyl group, n-propyl group, iso-propyl group, n-butyl group, iso-butyl group, t-butyl group, n-pentyl group, i-pentyl group, neopentyl group or n-hexyl group), an alkenyl group having two to six carbon atoms (e.g., vinyl group, allyl group, 1-propenyl group or isopropenyl group), an alkynyl group having two to six carbon atoms (e.g., ethynyl group, 1-propynyl group, 2-propynyl group, butynyl group, pentynyl group or hexynyl group), an alkoxy group having one to six carbon atoms (e.g., methoxy group, ethoxy group, n-propoxy group, iso-propoxy group or n-butoxy group) and an alkenyloxy group having two to six carbon atoms (e.g., vinyloxy group, allyloxy group, 1-propenyloxy group or isopropenyloxy group).

Preferred embodiments of the compound represented by the formula (I) according to the present invention, a salt thereof or a solvate of them are not specifically limited, of which more preferred embodiments are compounds wherein $R^4$ is 4-pyridyl group which may have one or two substituents, a salt thereof or a solvate of them.

The "salt" used in the present description is a salt formed from the compound according to the present invention, of which a pharmacologically acceptable salt is preferred. Preferred examples thereof are a hydrohalogenic acid salt such as hydrofluoride, hydrochloride, hydrobromide or hydroiodide; an inorganic acid salt such as sulfate, nitrate, perchlorate, phosphate, carbonates or hydrogencarbonate; an organic carboxylic acid salt such as acetate, trifluoroacetate, oxalate, maleate, tartrate, fumarate or citrate; an organic sulfonic acid salt such as methanesulfonate, trifluoromethanesulfonate, ethanesulfonate, benzenesulfonate, toluenesulfonate or camphorsulfonate; an amino acid salt such as aspartate or glutamate; a quaternary amine salt; an alkali metal salt such as sodium salt or potassium salt; an alkaline earth metal salt such as magnesium salt or calcium salt. More preferred examples of the "pharmacologically acceptable salt" are hydrochloride and oxalate.

The "solvate" used in the present description is a solvate of the compound according to the present invention or a salt thereof and is not specifically limited. Preferably, the solvate is a hydrate, a solvate with an alcohol such as methanol, ethanol, propanol, or isopropanol, a solvate with an ester such as ethyl acetate, a solvate with an ether such as methyl ether, ethyl ether or THF (tetrahydrofuran) or a solvate with DMF (dimethylformamide), of which a hydrate or a solvate with an alcohol such as methanol or ethanol is more preferred. A solvent for constituting the solvate is preferably a pharmacologically acceptable solvent.

Production Process

Typical production processes for the compounds represented by the formula (I) and the formula (IV) of the present invention will be illustrated below. The "room temperature" as used hereinafter represents a temperature from about 0° C. to about 40° C.

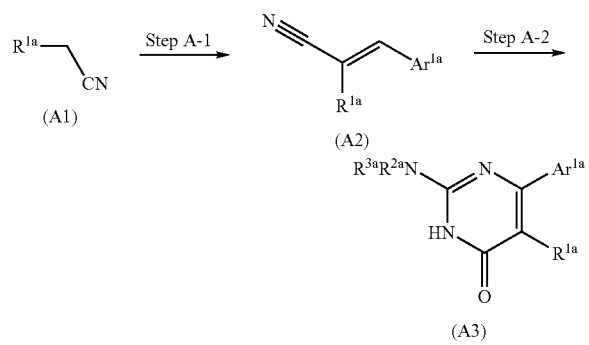

In the formula, $Ar^{1a}$ and $R^{1a}$ are the same as or different from each other and each represents an aromatic cyclic hydrocarbon group having six to fourteen carbon atoms which may be substituted or a 5 to 14-membered aromatic heterocyclic group which may be substituted; and $R^{2a}$ and $R^{3a}$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic cyclic hydrocarbon group having six to fourteen carbon atoms which may be substituted, or a 5 to 14-membered aromatic heterocyclic group which may be substituted.

Step A-1: In this process, the compound (A1) is subjected to dehydration-condensation with an aldehyde compound in the presence of a base, to give the compound (A2). The base for use in the reaction is preferably an alkali metal alkoxide, such as sodium methoxide, sodium ethoxide or potassium t-butoxide, and an alkali metal carbonate such as potassium carbonate or sodium carbonate may be also used. The reaction is performed in a solvent which does not adversely affect the reaction and dissolves the starting compounds and intermediates therein to some extent, such as ethanol, methanol, tetrahydrofuran, dichloromethane, chloroform, N,N-dimethylformamide, N-methylpyrrolidone, dimethyl sulfoxide, or a mixture of these solvents. The reaction is performed at 0° C. to 120° C.

Step A-2: In this process, the compound (A2) prepared in Process A-1 is reacted and cyclized with a guanidine derivative in the presence of a base and is aromatized with an oxidizing agent, to give the pyrimidinone derivative (A3) according to the present invention. The base for use in the cyclization is preferably an alkali metal alkoxide such as sodium methoxide, sodium ethoxide or potassium t-butoxide, and an alkali metal carbonate such as potassium carbonate or sodium carbonate may be also used. The oxidizing agent for the aromatization includes, for example, a manganese compound such as activated manganese dioxide; a quinone such as 2,3-dichloro-5,6-dicyano-1,4-benzoquinone; and sulfur. The solvent for use herein is not specifically limited, as long as it does not adversely affect the reaction and can dissolve the starting compounds and intermediates to some extent, and ethanol, methanol, tetrahydrofuran, dichloromethane, chloroform, N,N-dimethylformamide, N-methylpyrrolidone, dimethyl sulfoxide, or a mixture of these solvents are preferred. The reaction is performed at 0° C. to 120° C.

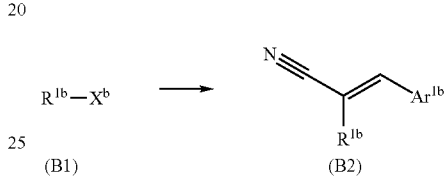

In the formula, $Ar^{1b}$ and $R^{1b}$ are the same as or different from each other and each represents an aromatic cyclic hydrocarbon group having six to fourteen carbon atoms which may be substituted or a 5 to 14-membered aromatic heterocyclic group which may be substituted; and $X^b$ represents a halogen atom, an alkylsulfonyloxy group or an arylsulfonyloxy group. This process is another synthetic process of the compound (A2) in Process A-1 of Production Process A. That is, the compound (B1) is reacted with a diester of cyanomethylphosphonic acid in the presence of a base and a palladium catalyst and is subjected to dephosphorylation-condensation with an aldehyde compound, to give the compound (B2). A suitable base for use in the reaction varies depending on, for example, the starting materials and the solvents, is not specifically limited, as long as it does not adversely affect the reaction, and is preferably sodium hydride. A suitable palladium catalyst for use herein varies depending on, for example, the starting materials and the solvent, is not specifically limited, as long as it does not adversely affect the reaction, and preferred examples thereof are tetrakis(triphenylphosphine)palladium(0), dichlorobis(triphenylphosphine)palladium(0) and tris(dibenzylideneacetone)dipalladium(0). A suitable reaction solvent for use herein varies depending on, for example, the starting materials and the reagent, is not specifically limited, as long as it does not adversely affect the reaction and can dissolve the starting materials therein to some extent, and is preferably an ether such as dimethoxyethane, diethyl ether or tetrahydrofuran. The reaction is performed at 0° C. to 120° C.

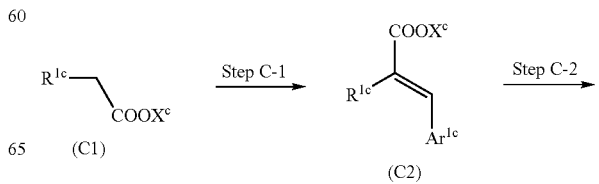

-continued

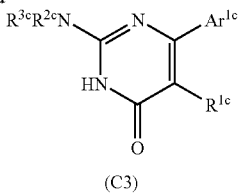

(C3)

In the formula, $Ar^{1c}$ and $R^{1c}$ are the same as or different from each other and each represents an aromatic cyclic hydrocarbon group having six to fourteen carbon atoms which may be substituted or a 5 to 14-membered aromatic heterocyclic group which may be substituted; $R^{2c}$ and $R^{3c}$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic cyclic hydrocarbon group having six to fourteen carbon atoms which may be substituted or a 5 to 14-membered aromatic heterocyclic group which may be substituted; and $X^c$ represents an alkyl group having one to six carbon atoms.

Step C-1: In this process, the compound (C1) is subjected to dehydration-condensation with an aldehyde compound using a carboxylic anhydride in the presence of a base, to give the compound (C2). A suitable base for use in the reaction varies depending on the starting materials and the solvents, is not specifically limited, as long as it does not adversely affect the reaction and includes, for example, an amine such as triethylamine, pyrrolidine, piperidine or diisopropylethylamine. As the carboxylic anhydride, acetic anhydride is preferred. The reaction is performed at a temperature from room temperature to 120° C.

Step C-2: In this process, the compound (C2) prepared in Process C-1 is reacted with a guanidine derivative in the presence of a base and is then aromatized using an oxidizing agent, to give the pyrimidinone derivative (C3) of the present invention. A suitable base for use in the reaction varies depending on the starting materials and the solvents, is not specifically limited, as long as it does not adversely affect the reaction, and includes an alkali metal alkoxide such as sodium methoxide, sodium ethoxide or potassium t-butoxide, as well as an alkali metal carbonate such as potassium carbonate or sodium carbonate. A suitable oxidizing agent for use in the reaction varies depending on the starting materials and the solvent, is not specifically limited, as long as it does not adversely affect the reaction and includes, for example, a manganese compound such as activated manganese dioxide; a quinone such as 2,3-dichloro-5,6-dicyano-1,4-benzoquinone; and sulfur. The reaction is performed in a solvent that does not adversely affect the reaction and dissolves the starting compounds and intermediates to some extent, such as ethanol, methanol, tetrahydrofuran, dichloromethane, chloroform, N,N-dimethylformamide, N-methylpyrrolidone, dimethyl sulfoxide, or a mixture of these solvents. The reaction is performed at 0° C. to 120° C.

(Production Process D)

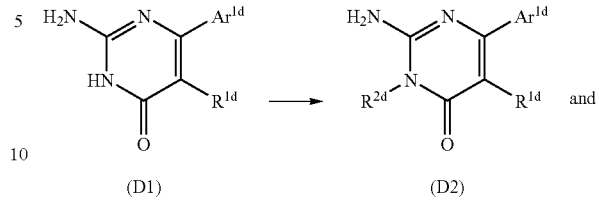

(D1)　　(D2)

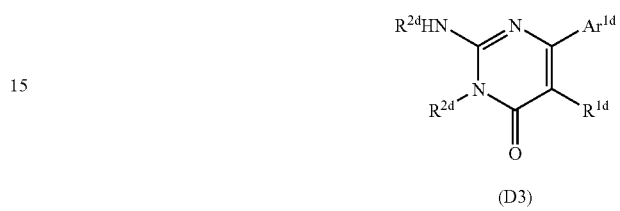

(D3)

In the formula, $Ar^{1d}$ and $R^{1d}$ are the same as or different from each other and each represents an aromatic cyclic hydrocarbon group having six to fourteen carbon atoms which may be substituted or a 5 to 14-membered aromatic heterocyclic group which may be substituted; and $R^{2d}$ represents an alkyl group having one to six carbon atoms which may be substituted, an alkenyl group having two to six carbon atoms which may be substituted or an alkynyl group having two to six carbon atoms which may be substituted. In this process, the nitrogen atom at the 3-position or the amino group at the 2-position of pyrimidine nucleus of the pyrimidinone derivative (D1) prepared in Production Process A or C is alkylated. The reaction is performed, for example, by reacting the compound with an alkyl halide compound in a solvent in the presence of a base.

A suitable base for use herein varies depending on the starting materials and the solvent, is not specifically limited, as long as it does not adversely affect the reaction and is preferably sodium hydride, sodium hydroxide, potassium hydroxide, sodium hydrogencarbonate, sodium carbonate or potassium carbonate. A suitable solvent for use herein varies depending on the starting materials and the reagent, is not specifically limited, as long as it dissolves the starting materials to some extent, and preferred examples thereof are an alcohol such as methanol or ethanol; an ether such as tetrahydrofuran, dioxane, dimethoxyethane or diethylene glycol dimethyl ether; as well as N,N-dimethylformamide, dimethyl sulfoxide, 1-methylpyrrolidinone. The reaction is performed at a temperature from 0° C. to 100° C.

(Production Process E)

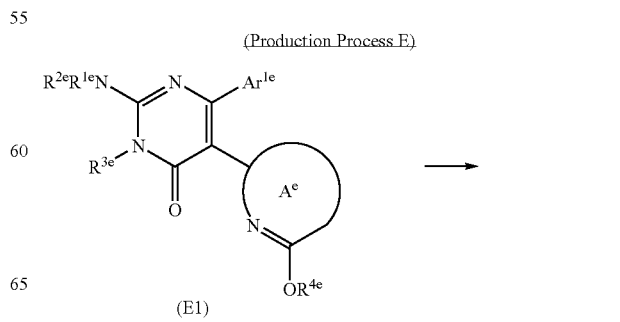

(E1)

-continued

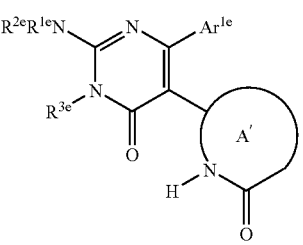

(E2)

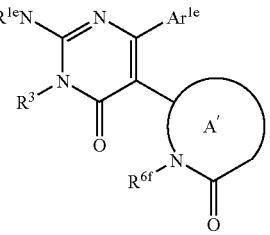

(F2)

In the formula, $Ar^{1e}$ represents an aromatic cyclic hydrocarbon group having six to fourteen carbon atoms which may be substituted or a 5 to 14-membered aromatic heterocyclic group which may be substituted; $R^{1e}$ and $R^{2e}$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic cyclic hydrocarbon group having six to fourteen carbon atoms which may be substituted, or a 5 to 14-membered aromatic heterocyclic group which may be substituted; $R^{3e}$ and $R^{4e}$ are the same as or different from each other and each represents a hydrogen atom, an alkyl group having one to six carbon atoms which may be substituted, an alkenyl group having two to six carbon atoms which may be substituted, or an alkynyl group having two to six carbon atoms which may be substituted; the ring $A^e$ represents pyridinyl group, pyrimidinyl group, pyrazinyl group or pyridazinyl group; and the ring A' represents dihydrooxopyridinyl group, dihydrooxopyrimidinyl group, dihydrooxopyrazinyl group or dihydrooxopyridazinyl group. In this process, the alkoxy group of the 5-(α-alkoxy-nitrogen-containing heteroaryl)pyrimidinone (E1) is hydrolyzed, to give 5-(α-oxo-nitrogen-containing heterocyclyl)pyrimidinone (E2) of to the present invention. The reaction is performed in an aqueous solution of a mineral acid such as hydrochloric acid, hydrobromic acid or sulfuric acid or a mixture of the aqueous solution of the mineral acid with acetic acid at a temperature from room temperature to 100° C.

In the formula, $Ar^{1e}$, $R^{1e}$, $R^{2e}$, $R^{3e}$ and the ring A' have the same meanings as defined in Production Process E; $R^{6f}$ represents, for example, an alkyl group having one to six carbon atoms which may be substituted, an alkenyl group having two to six carbon atoms which may be substituted or an alkynyl group having two to six carbon atoms which may be substituted; and $X^f$ represents a halogen atom, an alkylsulfonyloxy group or an arylsulfonyloxy group. In this process, the compound (F2) having a substituent introduced into the nitrogen atom on the ring A' of the present invention can be prepared by reacting compound (F1) with an alkyl halide compound and so on in a solvent in the presence of base. A suitable base for use herein varies depending on the starting materials and the solvent, is not specifically limited, as long as it does not adversely affect the reaction and includes sodium hydride, sodium hydroxide, potassium hydroxide, sodium hydrogencarbonate, sodium carbonate or potassium carbonate. A suitable solvent for use herein varies depending on the starting materials and the reagent, is not specifically limited, as long as it does not adversely affect the reaction and dissolves the starting materials to some extent, and includes an alcohol such as methanol or ethanol; an ether such as tetrahydrofuran, dioxane, dimethoxyethane or diethylene glycol dimethyl ether; as well as N,N-dimethylformamide, dimethyl sulfoxide or 1-methylpyrrolidinone. The reaction is generally performed at a temperature from 0° C. to 100° C.

(Production Process G)

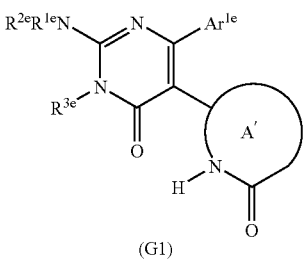

(G1)

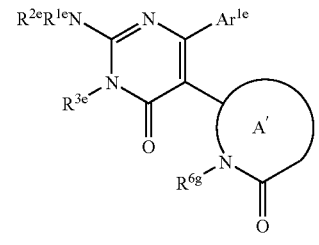

(G2)

(Production Process F)

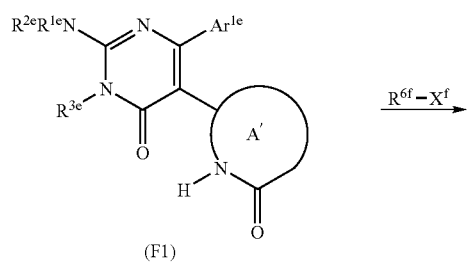

(F1)

In the formula, $Ar^{1e}$, $R^{1e}$, $R^{2e}$, $R^{3e}$ and the ring A' have the same meanings as defined in Production Process E; and $R^{6g}$ represents an aromatic cyclic hydrocarbon group having six to fourteen carbon atoms which may be substituted, a 5 to 14-membered aromatic heterocyclic group which may be substituted or an alkenyl group having two to six carbon atoms which may be substituted. The compound (G2) according to the present invention can be prepared by reacting the compound (G1) with an arylboron reagent, heteroarylboron reagent or alkenylboron reagent in a solvent in the presence of a base and a copper catalyst. A suitable base for use in the reaction varies depending on the starting materials and the solvent, is not specifically limited, as long as it does not adversely affect the reaction, and is preferably a tertiary amine such as pyridine, diisopropylethylamine or triethylamine. A suitable copper catalyst for use herein varies depending on the starting materials and the solvent, is not specifically limited, as long as it does not adversely affect the reaction, is preferably a divalent copper compound such as cupric acetate, cupric bromide or cupric sulfate and is more preferably cupric acetate. A suitable solvent for use herein varies depending on the starting materials and the reagent, is not specifically limited, as long as it does not adversely affect the reaction and dissolves the starting materials to some extent, and is preferably, for example N,N-dimethylformamide, tetrahydrofuran, ethyl acetate or dichloromethane. The reaction temperature is preferably from 0° C. to 120° C.

Typical examples of the production processes for the compounds (I) according to the present invention have been illustrated above. The material compounds used in the production of the compounds of the present invention may form salts and/or solvates and are not specifically limited, as long as they do not adversely affect the reaction. When the compounds (I) according to the present invention are obtained as free compounds, they can be converted into possible salts of the above-mentioned compounds (I) according to a conventional procedure. Various isomers such as geometrical isomers, optical isomers based on an asymmetric carbon, rotational isomers, stereoisomers, and tautomers obtained as the compounds (I) according to the present invention can be purified and isolated according to a conventional separation means. Such separation means include, for example, recrystallization, diastereomeric salt method, enzymatic resolution, and a variety of chromatography such as thin layer chromatography, column chromatography or gas chromatography.

The compounds represented by the formula (I) according to the present invention, salts thereof or solvates of them can be formulated into pharmaceutical preparations as intact or as a mixture with, for example, a known pharmacologically acceptable carrier according to a conventional procedure. Preferred dosage forms are tablets, powders, subtle granules, granules, coated tablets, capsules, syrups, troches, inhalants, suppositories, injections, ointments, ophthalmic ointments, eye drops, nasal drops, ear drops, cataplasms, and lotions. In the formulation, generally used fillers, binders, disintegrators, lubricants, coloring agents, and flavoring agents, as well as stabilizers, emulsifiers, absorbefacients, surfactants, pH adjusting agents, antiseptics, and antioxidants according to necessity can be used. They can be formulated according to a conventional procedure using components generally used as raw materials for pharmaceutical preparations. Examples of such components include (1) animal and vegetable oils such as soybean oil, beef tallow and synthetic glycerides; (2) hydrocarbons such as liquid paraffins, squalane and solid paraffins; (3) ester oils such as octyldodecyl myristate and isopropyl myristate; (4) higher alcohols such as cetostearyl alcohol and behenyl alcohol; (5) silicone resins; (6) silicone oils; (7) surfactants such as polyoxyethylene fatty acid esters, sorbitan fatty acid esters, glycerin fatty acid esters, polyoxyethylene sorbitan fatty acid esters, polyoxyethylene hydrogenated castor oils and polyoxyethylene-polyoxypropylene block copolymers; (8) water-soluble polymers such as hydroxyethyl cellulose, poly (acrylic acid)s, carboxyvinyl polymers, polyethylene glycol, polyvinylpyrrolidone and methylcellulose; (9) lower alcohols such as ethanol and isopropanol; (10) polyhydric alcohols such as glycerol, propylene glycol, dipropylene glycol and sorbitol; (11) sugars such as glucose and sucrose; (12) inorganic powders such as silicic anhydride, magnesium aluminium silicate and aluminium silicate; and (13) purified water. 1) The fillers include, for example, lactose, corn starch, sucrose, glucose, mannitol, sorbitol, crystalline cellulose and silicon dioxide; 2) the binders include, for example, polyvinyl alcohol, polyvinyl ether, methylcellulose, ethylcellulose, gum arabic, gum tragacanth, gelatin, shellac, hydroxypropyl cellulose, hydroxypropylmethyl cellulose, polyvinylpyrrolidone, polypropylene glycol-polyoxyethylene block polymers, meglumine, calcium citrate, dextrin and pectin; 3) the disintegrators include, for example, starch, agar, gelatin powder, crystalline cellulose, calcium carbonate, sodium hydrogencarbonate, calcium citrate, dextrin, pectin and carboxymethylcellulose calcium; 4) the lubricants include, for example, magnesium stearate, talc, polyethylene glycol, silica, and hardened vegetable oils; 5) the coloring agents can be any coloring agents which are approved to add to pharmaceutical preparations; 6) the flavoring agents include, for example, cocoa powder, menthol, aromatic powder (empasm), peppermint oil, camphol (borneol) and cinnamon powder; and 7) the antioxidants can be any antioxidants which are approved to add to pharmaceutical preparations, such as ascorbic acid and α-tocopherol.

1) The oral preparation is produced by mixing the compound according to the present invention, a salt thereof or a solvate of them with a filler, and if necessary, a binder, disintegrator, lubricant, coloring agent, flavoring agent, and other components, and formulating the mixture according to a conventional procedure into, for example, a powder, subtle granules, granules, tablet, coated tablet or capsules. 2) The tablets and granules can be appropriately coated with, for example, sugar or gelatin according to necessity. 3) The liquid formulations such as syrups, injection preparations or eye drops can be prepared according to a conventional procedure by adding a pH adjusting agent, solubilizer, and isotonizing agent, and if necessary, a solubilizing agent, stabilizer, buffer, suspending agent, antioxidant, and other components. The liquid formulations can also be formed into freeze-dried products. The injections can be administered intravenously, subcutaneously and/or intramuscularly. Preferred examples of the suspending agents are methylcellulose, polysorbate 80, hydroxyethyl cellulose, gum arabic, powdered tragacanth, carboxymethylcellulose sodium and polyoxyethylene sorbitan monolaurate; preferred examples of the solubilizers are polyoxyethylene hydrogenated caster oil, polysorbate 80, nicotinamide and polyoxyethylene sorbitan monolaurate; preferred examples of the stabilizers are sodium sulfite, sodium metasulfite and ether; preferred examples of the preservatives are methyl p-hydroxybenzoate, ethyl p-hydroxybenzoate, sorbic acid, phenol, cresol and chlorocresol. 4) The external preparations can be produced according to a conventional procedure not specifically limited. Base materials for use herein can be any raw materials generally used in, for example, pharmaceutical preparations, quasi drugs and cosmetics. Such raw materials include, for example, animal and vegetable oils, mineral oils, ester oils, waxes, higher alcohols, fatty acids, silicone oils, surfactants, phospholipids, alcohols, polyhydric alcohols, water-soluble polymers, clay minerals, and purified water. Where necessary, any of pH adjusting agents, antioxidants, chelating agents, antiseptics and antimolds, coloring agents, flavors, and others can be added. In addition, components having differentiation-inducing action, blood-flow accelerators, bactericides, anti-inflammatory agents, cell activators, vitamins, amino acids, humectants, keratolytic agents, and other components can be added according to necessity.

The dose of the pharmaceutical preparation according to the present invention varies depending on the degree of symptom, age, sex, body weight, administration mode, type of the salt, difference in sensibility to the drug, concrete type of the disease and other factors. Generally, the pharmaceutical preparation may be administered to an adult in one to several divided doses at a daily dose of about 30 μg to about 10 g, preferably 100 μg to 5 g, and more preferably 100 μg to 100 mg for oral administration, or about 30 μg to about 1 g, preferably 100 μg to 500 mg, and more preferably 100 μg to 30 mg for injection administration.

The present invention can provide novel pyrimidone compounds. The compounds according to the present invention, salts thereof or solvates of them have excellent antagonism against adenosine receptors (adenosine $A_1$, $A_{2A}$, $A_{2B}$ or $A_3$ receptor) and are specifically excellent as an antagonist against the adenosine $A_2$ receptors, specifically against the adenosine $A_{2B}$ receptor. They are useful as an agent for treating or preventing a disease to which the adenosine receptors (adenosine $A_1$, $A_{2A}$, $A_{2B}$ or $A_3$ receptor) relate and a disease against which an antagonist of the receptor is efficacious. They are useful as an agent for treating, preventing or improving, for example, constipation, irritable bowel syndrome, constipation accompanying irritable bowel syndrome, organic constipation, constipation accompanying enteroparalytic ileus, constipation accompanying congenital digestive tract dysfunction, constipation accompanying ileus, diabetes mellitus, diabetic complications, diabetic retinopathy, obesity or asthma and are also useful as, for example, a hypoglycemic agent, agent for ameliorating glucose intolerance, insulin sensitizer, antihypertensive drug, diuretic agent, agent for treating osteoporosis, agent for treating Parkinson's disease, agent for treating Alzheimer's disease, agent for treating an inflammatory bowel disease or agent for treating Crohn's disease.

EXAMPLES

The following Referential Examples, Examples and Test Examples are illustrative, and the compounds of the present invention are under no circumstances restricted by the following examples. Those skilled in the art can modify not only the following Examples but also the claims according to the present description in various ways to exploit to the full of the present invention, and such modifications and variations are also included within the scope of the appended claims relating to the present description.

Referential Example 1

Ethyl (E)-3-(3-fluorophenyl)-2-(4-pyridyl)-2-propenoate

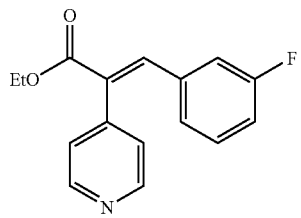

A solution of ethyl 4-pyridylacetate (25.0 g, 0.151 mol) and 3-fluorobenzaldehyde (20.7 g, 0.167 mol) in a mixture of acetic anhydride (100 mL) and triethylamine (20 mL) was heated under reflux for 5.5 hours. After standing to cool, the reaction mixture was concentrated. The residue was diluted with ethyl acetate and a saturated aqueous sodium hydrogencarbonate solution, and the aqueous layer was extracted with ethyl acetate. The combined organic layers were washed with a saturated aqueous sodium hydrogencarbonate solution twice and brine, dried over anhydrous sodium sulfate and then concentrated. The residue was subjected to silica gel column chromatography (eluent; hexane, hexane:ethyl acetate=9:1), to give the title compound (25.5 g, 62%) as a red-orange oil.

$^1$H NMR (400 MHz, CDCl$_3$) δ ppm; 1.28 (3H, t, J=7.2 Hz), 4.27 (2H, q, J=7.2 Hz), 6.70–6.75 (1H, m), 6.80–6.84 (1H, m), 6.91–6.97 (1H, m), 7.12–7.18 (1H, m), 7.16 (2H, dd, J=1.6, 4.4 Hz), 7.85 (1H, s), 8.62 (2H, dd, J=1.6, 4.4 Hz).

Referential Example 2

Ethyl (E)-3-(2-furyl)-2-(4-pyridyl)-2-propenoate

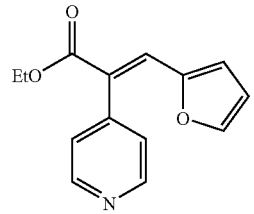

The title compound was synthesized in a manner similar to that described for the method of Referential Example 1 using 2-furaldehyde.

$^1$H NMR (400 MHz, CDCl$_3$) δ ppm; 1.20 (3H, t, J=7.2 Hz), 4.18 (2H, q, J=7.2 Hz), 6.51 (1H, d, J=3.6 Hz), 6.54 (1H, dd, J=1.6, 3.6 Hz), 7.29 (2H, dd, J=1.6, 4.4 Hz), 7.66 (1H, s), 7.69 (1H, d, J=1.6 Hz), 8.62 (2H, dd, J=1.6, 4.4 Hz).

Referential Example 3

(E)-3-(3-Fluorophenyl)-2-(4-pyridyl)-2-propenenitrile

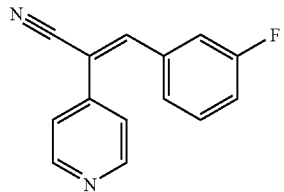

Sodium (3.0 g, 130 mmol) was dissolved in ethanol (150 mL), 4-pyridylacetonitrile hydrochloride (10 g, 65 mmol) was added thereto, and then the mixture was stirred at room temperature. After 10 minutes, 3-fluorobenzaldehyde (8 g, 65 mmol) was added thereto, followed by stirring as it was for 30 minutes. The resulting precipitates were collected by filtration and washed with a small portion of water, to give the title compound (8.2 g, 56%) as a colorless solid.

$^1$H NMR (400 MHz, DMSO-d$_6$) δ ppm; 7.40–7.46 (1H, m), 7.61–7.68 (1H, m), 7.75 (2H, dd, J=1.6, 4.4 Hz), 7.77–7.86 (2H, m), 8.37 (1H, s), 8.73 (2H, dd, J=1.6, 4.4 Hz).

Referential Example 4

(E)-3-(3-Fluorophenyl)-2-(6-methoxy-3-pyridyl)-2-propenenitrile

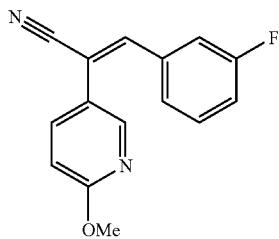

To a suspension of sodium hydride (8.8 g, 0.220 mol) in 1,2-dimethoxyethane (300 mL) was gradually added diethyl cyanomethylphosphonate (19.7 g, 0.122 mol) at room temperature under an atmosphere of nitrogen gas. After stirring for 15 minutes, 5-bromo-2-methoxypyridine (20.0 g, 0.106 mol) and tetrakis(triphenylphosphine)palladium(0) (2.0 g, 1.73 mmol) were sequentially added thereto, and the mixture was heated to 90° C. and stirred for 6 hours. After standing to cool, the reaction mixture was further cooled on ice. 3-Fluorobenzaldehyde (13.7 g, 0.110 mol) was added dropwise thereinto under an atmosphere of nitrogen gas at 1° C. to 4° C. over 1.5 hours, and the mixture was stirred for further 2.5 hours while gradually elevating to room temperature. The reaction mixture was diluted with a saturated aqueous ammonium chloride solution and ethyl acetate, and then the aqueous layer was extracted with ethyl acetate. The combined organic layers were washed with a saturated aqueous ammonium chloride solution twice, dried over anhydrous sodium sulfate and then concentrated. The residue was suspended in methanol, and the resulting solid was collected by filtration and washed with diethyl ether and hexane, to give the title compound (7.80 g, 29%) as a colorless solid.

$^1$H NMR (400 MHz, DMSO-$d_6$) δ ppm; 3.92 (3H, s), 7.00 (1H, d, J=8.8 Hz), 7.34–7.40 (1H, m), 7.57–7.64 (1H, m), 7.69–7.78 (2H, m), 8.03 (1H, s), 8.11 (1H, dd, J=2.6, 8.8 Hz), 8.53 (1H, d, J=2.6 Hz).

Referential Example 5

(E)-3-(2-Furyl)-2-(6-methoxy-3-pyridyl)-2-propenenitrile

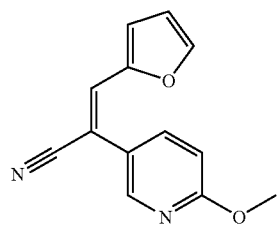

The title compound was obtained (16.3 g, 68%) as a yellow solid in a manner similar to that described for Referential Example 4 from furfural instead of 3-fluorobenzaldehyde.

$^1$H NMR (400 MHz, DMSO-$d_6$) δ ppm; 3.90 (3H, s), 6.75 (1H, dd, J=1.6, 3.6 Hz), 6.94 (1H, dd, J=0.8, 8.8 Hz), 7.11 (1H, dd, J=0.8, 3.6 Hz), 7.83 (1H, s), 8.00 (1H, dd, J=0.8, 1.6 Hz), 8.04 (1H, dd, J=2.8, 8.8 Hz), 8.46 (1H, dd, J=0.8, 2.8 Hz).

Example 1

2-Amino-6-(3-fluorophenyl)-5-(4-pyridyl)-3,4-dihydro-4-pyrimidinone

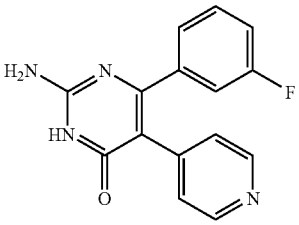

(Method 1)

Sodium (3.2 g, 139 mmol) was dissolved in ethanol (200 mL), and then 4-pyridylacetonitrile (10.0 g, 64.7 mmol), 3-fluorobenzaldehyde (7.3 mL, 68.8 mmol) and guanidine hydrochloride (7.0 g, 73.3 mmol) were successively added thereto under ice-cooling, followed by heating under reflux for two days. The insoluble matters were filtered off, and the filtrate was concentrated. The residue was subjected to silica gel column chromatography (eluent; dichloromethane, dichloromethane:methanol=20:1, 10:1, 5:1), to give the 5,6-dihydro form of the title compound (13.6 g) as a crude product. To the crude product was added sulfur (26.4 g, 82.3 mmol in terms of sulfur), followed by heating at 185° C. for 2.5 hours. After standing to cool, the reaction mixture was suspended in methanol. The insoluble matters were filtered off and washed with 2N hydrochloric acid. After concentrating methanol from the filtrate, the residue was washed with ethyl acetate twice. The aqueous layer was adjusted to pH 11 with a 5N aqueous sodium hydroxide solution, and washed with ethyl acetate twice. The aqueous layer was neutralized with 2N hydrochloric acid, and the resulting crystals were collected by filtration, and washed with water and ethyl acetate, to give the title compound (6.2 g, 34%) as a colorless solid. In this process, the title compound could also be obtained by isolating (E)-3-(3-fluorophenyl)-2-(4-pyridyl)-2-propenenitrile and then subjecting it to cyclization reaction with guanidine in a manner similar to that described for Referential Example 3.

(Method 2)

Sodium (3.4 g, 147 mmol) was dissolved in ethanol (500 mL), and ethyl (E)-3-(3-fluorophenyl)-2-(4-pyridyl)-2-propenoate (33 g, 121 mmol) and guanidine hydrochloride (13.9 g, 146 mmol) were added thereto, followed by heating under reflux for 13 hours. After standing to cool, the solvent was removed and to the residue was added tetrahydrofuran (500 mL). The insoluble matters were filtered off, and the filtrate was concentrated. To a solution of the residue in tetrahydrofuran (1500 mL) and methanol (100 mL) was added activated manganese dioxide (250 g), followed by heating under reflux. After 2 hours, additional activated manganese dioxide (100 g) was added and the mixture was heated under reflux further for one and a quarter hour. After standing to cool, manganese dioxide was filtered off through Celite, and washed with tetrahydrofuran and methanol. The combined filtrates were concentrated, and to the residue was added acetonitrile. The resulting precipitates were collected by filtration, to give the title compound (15 g, 44%) as a yellow powder.

$^1$H NMR (400 MHz, DMSO-d$_6$) δ ppm; 6.86 (2H, br s), 6.96 (1H, d, J=7.6 Hz), 7.00–7.07 (3H, m), 7.00–7.15 (1H, m), 7.20–7.28 (1H, m), 8.34 (2H, d, J=3.2 Hz); MS m/e (ESI) 283 (MH$^+$).

Example 2

2-Amino-6-(2-furyl)-5-(4-pyridyl)-3,4-dihydro-4-pyrimidinone

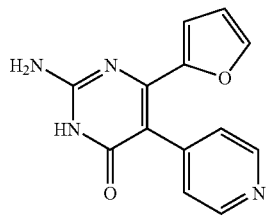

The title compound was synthesized in a manner similar to that described for the Method 1 of Example 1 from 2-furaldehyde.

$^1$H NMR (400 MHz, DMSO-d$_6$) δ ppm; 6.48 (1H, dd, J=1.6, 3.6 Hz), 6.54 (1H, dd, J=0.8, 3.6 Hz), 6.91 (2H, br s), 7.21 (2H, dd, J=1.6, 4.6 Hz), 7.54 (1H, dd, J=0.8, 1.6 Hz), 8.52 (2H, dd, J=1.6, 4.6 Hz); MS m/e (ESI) 255 (MH$^+$).

Examples 3 and 4

Example 3

2-Amino-6-(3-fluorophenyl)-3-methyl-5-(4PCT pyridyl)-3,4-dihydro-4-pyrimidinone

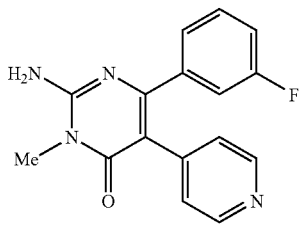

Example 4

6-(3-Fluorophenyl)-3-methyl-2-(methylamino)-5-(4-pyridyl)-3,4-dihydro-4-pyrimidinone

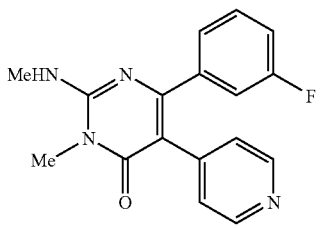

To a solution of 2-amino-6-(3-fluorophenyl)-5-(4-pyridyl)-3,4-dihydro-4-pyrimidinone (100 mg, 0.354 mmol) in N,N-dimethylformamide (2 mL) was added sodium hydride (15 mg, 0.375 mmol in terms of 60% suspension) at 0° C. under an atmosphere of nitrogen gas, followed by stirring. After 10 minutes, iodomethane (30 μL, 0.482 mmol) was added thereto, followed by stirring further for 30 minutes. The reaction mixture was diluted with ethyl acetate and a saturated aqueous ammonium chloride solution. The organic layer was washed with a saturated aqueous ammonium chloride solution, water and brine, dried over anhydrous sodium sulfate and then concentrated. The residue was subjected to silica gel plate (developing solvent; dichloromethane:methanol=10:1), to give 2-amino-6-(3-fluorophenyl)-3-methyl-5-(4-pyridyl)-3,4-dihydro-4-pyrimidinone (19 mg, 18%) and 6-(3-fluorophenyl)-3-methyl-2-(methylamino)-5-(4-pyridyl)-3,4-dihydro-4-pyrimidinone (6 mg, 5%) as a colorless solid, respectively.

2-Amino-6-(3-fluorophenyl)-3-methyl-5-(4-pyridyl)-3,4-dihydro-4-pyrimidinone $^1$H NMR (400 MHz, DMSO-d$_6$) δ ppm; 3.36 (3H, s), 6.93–7.16 (3H, m), 7.04 (2H, d, J=4.8 Hz), 7.20–7.29 (1H, m), 7.50 (2H, br s), 8.35 (2H, d, J=4.8 Hz); MS m/e (ESI) 297 (MH$^+$).

6-(3-Fluorophenyl)-3-methyl-2-(methylamino)-5-(4-pyridyl)-3,4-dihydro-4-pyrimidinone $^1$H NMR (400 MHz, DMSO-d$_6$) δ ppm; 2.93 (3H, d, J=4.4 Hz), 3.35 (3H, s), 6.99–7.16 (3H, m), 7.05 (2H, d, J=5.8 Hz), 7.22–7.29 (1H, m), 7.49 (1H, q, J=4.4 Hz), 8.37 (2H, d, J=5.8 Hz); MS m/e (ESI) 311 (MH$^+$).

Example 5

2-Amino-3-ethyl-6-(3-fluorophenyl)-5-(4-pyridyl)-3,4-dihydro-4-pyrimidinone

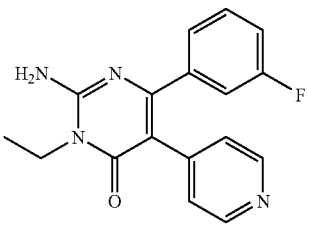

The title compound was synthesized in a manner similar to that described for Example 3 from ethyl iodide.

$^1$H NMR (400 MHz, DMSO-d$_6$) δ ppm; 1.19 (3H, t, J=7.2 Hz), 3.99 (2H, q, J=7.2 Hz), 6.94–6.99 (1H, m), 7.01–7.14 (2H, m), 7.05 (2H, d, J=5.6 Hz), 7.21–7.28 (1H, m), 7.53 (2H, br s), 8.35 (2H, d, J=5.6 Hz); MS m/e (ESI) 311 (MH$^+$).

Example 6

2-Amino-6-(3-fluorophenyl)-3-propyl-5-(4-pyridyl)-3,4-dihydro-4-pyrimidinone

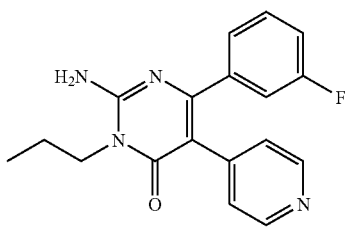

The title compound was synthesized in a manner similar to that described for Example 3 from n-propyl iodide.

$^1$H NMR (400 MHz, DMSO-d$_6$) δ ppm; 0.90 (3H, t, J=7.6 Hz), 1.58 (2H, sex, J=7.6 Hz), 3.85 (2H, t, J=7.6 Hz), 6.93–7.16 (3H, m), 7.04 (2H, d, J=5.2 Hz), 7.19–7.28 (1H, m), 7.52 (2H, br s), 8.34 (2H, d, J=5.2 Hz); MS m/e (ESI) 325 (MH$^+$).

Example 7

2-Amino-6-(2-furyl)-3-methyl-5-(4-pyridyl)-3,4-dihydro-4-pyrimidinone

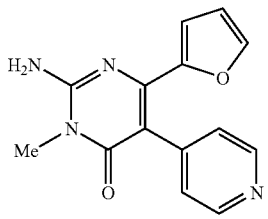

The title compound was synthesized in a manner similar to that described for Example 3 from 2-amino-6-(2-furyl)-5-(4-pyridyl)-3,4-dihydro-4-pyrimidinone.

$^1$H NMR (400 MHz, DMSO-d$_6$) δ ppm; 3.32 (3H, s), 6.42 (1H, d, J=3.6 Hz), 6.46 (1H, dd, J=1.6, 3.6 Hz), 7.14 (2H, d, J=4.6 Hz), 7.39 (2H, br s), 7.55 (1H, s), 8.50 (2H, d, J=4.6 Hz); MS m/e (ESI) 269 (MH$^+$).

Example 8

2-Amino-3-ethyl-6-(2-furyl)-5-(4-pyridyl)-3,4-dihydro-4-pyrimidinone

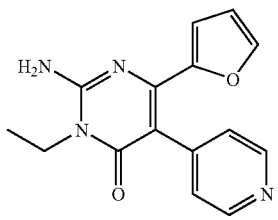

The title compound was synthesized in a manner similar to that described for Example 3 from 2-amino-6-(2-furyl)-5-(4-pyridyl)-3,4-dihydro-4-pyrimidinone and ethyl iodide.

$^1$H NMR (400 MHz, DMSO-d$_6$) δ ppm; 1.15 (3H, t, J=7.2 Hz), 3.95 (2H, q, J=7.2 Hz), 6.42 (1H, dd, J=0.8, 3.6 Hz), 6.46 (1H, dd, J=1.6, 3.6 Hz), 7.15 (2H, dd, J=1.6, 4.4 Hz), 7.24 (2H, br s), 7.55 (1H, dd, J=0.8, 1.6 Hz), 8.49 (2H, dd, J=1.6, 4.4 Hz); MS m/e (ESI) 283 (MH$^+$).

Example 9

2-Amino-6-(2-furyl)-3-propyl-5-(4-pyridyl)-3,4-dihydro-4-pyrimidinone

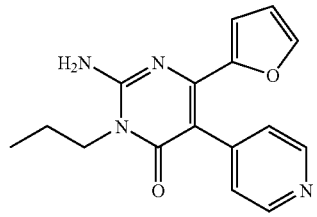

The title compound was synthesized in a manner similar to that described for Example 3 from 2-amino-6-(2-furyl)-5-(4-pyridyl)-3,4-dihydro-4-pyrimidinone and n-propyl iodide.

$^1$H NMR (400 MHz, DMSO-d$_6$) δ ppm; 0.90 (3H, t, J=7.6 Hz), 1.58 (2H, sex, J=7.6 Hz), 3.85 (2H, t, J=7.6 Hz), 6.43 (1H, dd, J=0.8, 3.6 Hz), 6.45 (1H, dd, J=1.6, 3.6 Hz), 7.14 (2H, dd, J=1.2, 4.4 Hz), 7.40 (2H, br s), 7.55 (1H, dd, J=0.8, 1.6 Hz), 8.54 (2H, dd, J=1.2, 4.4 Hz); MS m/e (ESI) 297 (MH$^+$).

Example 10

3-allyl-2-amino-6-(2-furyl)-5-(4-pyridyl)-3,4-dihydro-4-pyrimidinone

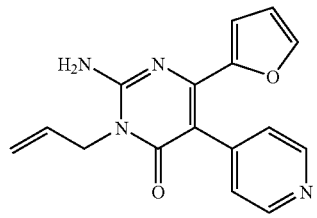

The title compound was synthesized in a manner similar to that described for Example 3 from 2-amino-6-(2-furyl)-5-(4-pyridyl)-3,4-dihydro-4-pyrimidinone and allyl bromide.

$^1$H NMR (400 MHz, DMSO-d$_6$) δ ppm; 4.57 (2H, d, J=5.0 Hz), 5.12–5.20 (2H, m), 5.85 (1H, ddt, J=5.0, 10.4, 17.2 Hz), 6.45 (1H, d, J=3.2 Hz), 6.47 (1H, dd, J=1.6, 3.2 Hz), 7.15 (2H, dd, J=1.2, 4.8 Hz), 7.34 (2H, br s), 7.56 (1H, d, J=1.6 Hz), 8.49 (2H, dd, J=1.2, 4.8 Hz); MS m/e (FAB) 295 (MH$^+$).

Example 11

2-Amino-6-(3-fluorophenyl)-5-(6-methoxy-3-pyridyl)-3,4-dihydro-4-pyrimidinone

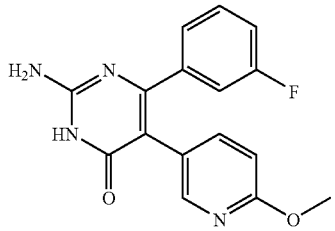

The title compound was synthesized in a manner similar to that described for the Method 2 of Example 1 from (E)-3-(3-fluorophenyl)-2-(6-methoxy-3-pyridyl)-2-propenenitrile.

$^1$H NMR (400 MHz, DMSO-$d_6$) δ ppm; 3.77 (3H, s), 6.66 (1H, dd, J=0.8, 8.4 Hz), 6.76 (2H, brs), 6.96–6.98 (1H, m), 7.02–7.09 (2H, m), 7.21–7.25 (1H, m), 7.37 (1H, dd, J=2.4, 8.4 Hz), 7.72 (1H, dd, J=0.8, 2.4 Hz), 11.29 (1H, brs).

Example 12

2-Amino-6-(3-fluorophenyl)-5-(6-methoxy-3-pyridyl)-3-methyl-3,4-dihydro-4-pyrimidinone

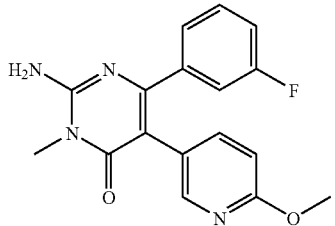

To a solution of 2-amino-6-(3-fluorophenyl)-5-(6-methoxy-3-pyridyl)-3,4-dihydro-4-pyrimidinone (1.0 g, 3.2 mmol) in N,N-dimethylformamide (3 mL) was added sodium hydride (77 mg, 3.2 mmol). After stirring for 10 minutes, iodomethane (454 mg, 0.2 mL, 3.2 mmol) was added thereto, and the mixture was stirred at room temperature for 2 hours. After removing the solvent from the reaction mixture, the residue was washed with water, to give the title compound (600 mg).

$^1$H NMR (400 MHz, DMSO-$d_6$) δ ppm; 3.32 (3H, s), 3.78 (3H, s), 6.68 (1H, dd, J=0.8, 8.8 Hz), 6.97–7.12 (3H, m), 7.23–7.28 (1H, m), 7.36 (2H, brs), 7.39 (1H, dd, J=2.4, 8.8 Hz), 7.74 (1H, dd, J=0.8, 2.4 Hz).

Example 13

2-Amino-6-(3-fluorophenyl)-3-methyl-5-(6-oxo-1,6-dihydro-3-pyridinyl)-3,4-dihydro-4-pyrimidinone

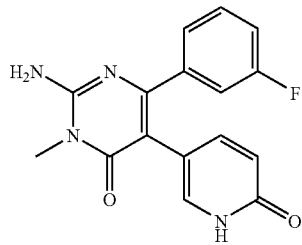

In a mixture solution of acetic acid and 48% hydrogen bromide, 2-amino-6-(3-fluorophenyl)-5-(6-methoxy-3-pyridyl)-3-methyl-3,4-dihydro-4-pyrimidinone was stirred at 100° C. for 2 hours. After cooling, the reaction solution was basified and washed with ethyl acetate. The aqueous layer was neutralized with diluted hydrochloric acid, and the resulting solid was collected by filtration, to give the title compound.

$^1$H NMR (400 MHz, DMSO-$d_6$-$D_2O$) δ ppm; 3.33 (3H, s), 6.17 (1H, d, J=9.4 Hz), 6.94 (1H, d, J=2.4 Hz), 7.09 (1H, dd, J=2.4, 9.4 Hz), 7.11–7.14 (3H, m), 7.28–7.35 (1H, m).

Example 14

2-Amino-6-(3-fluorophenyl)-3-methyl-5-(1-methyl-6-oxo-1,6-dihydro-3-pyridinyl)-3,4-dihydro-4-pyrimidinone

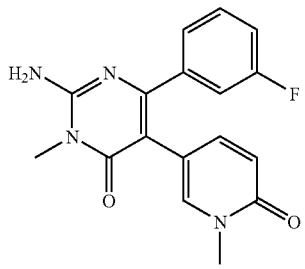

To a solution of 2-amino-6-(3-fluorophenyl)-3-methyl-5-(6-oxo-1,6-dihydro-3-pyridinyl)-3,4-dihydro-4-pyrimidinone (20 mg, 0.06 mmol) in dimethyl sulfoxide (1 mL) were added potassium carbonate (20 mg, 0.12 mmol) and iodomethane (20 μL, 0.30 mmol), followed by stirring at 50° C. for 16 hours. After filtering off the insoluble matters, the filtrate was purified by HPLC, to give the title compound (4 mg).

$^1$H NMR (400 MHz, $CD_3OD$) δ ppm; 3.47 (3H, s), 3.48 (3H, s), 6.39 (1H, d, J=9.2 Hz), 7.02–7.08 (1H, m), 7.12–7.20 (3H, m), 7.26–7.31 (1H, m), 7.42 (1H, d, J=2.4 Hz).

Example 15

2-Amino-5-(1-ethyl-6-oxo-1,6-dihydro-3-pyridinyl)-6-(3-fluorophenyl)-3-methyl-3,4-dihydro-4-pyrimidinone

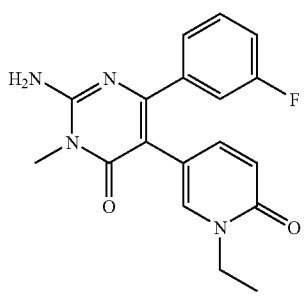

The title compound was obtained in a manner similar to that described for Example 14 from iodoethane.

$^1$H NMR (400 MHz, $CD_3OD$) δ ppm; 1.12 (3H, t, J=7.2 Hz), 3.48 (3H, s), 3.88 (2H, q, J=7.2 Hz), 6.44 (1H, dd, J=0.8, 9.2 Hz), 7.02–7.07 (1H, m), 7.10–7.16 (2H, m), 7.27–7.28 (2H, m), 7.31 (1H, dd, J=2.4, 9.2 Hz).

Example 16

2-Amino-6-(3-fluorophenyl)-3-methyl-5-(6-oxo-1-propyl-1,6-dihydro-3-pyridinyl)-3,4-dihydro-4-pyrimidinone

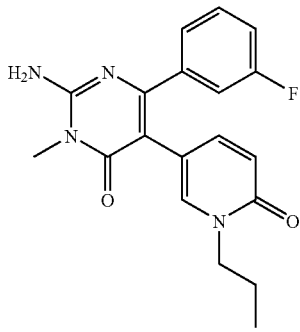

The title compound was obtained in a manner similar to that described for Example 14 from 1-iodopropane.

$^1$H NMR (400 MHz, CD$_3$OD) δ ppm; 0.76 (3H, t, J=7.2 Hz), 1.53 (2H, tq, J=7.2, 7.2 Hz), 3.48 (3H, s), 3.81 (2H, t, J=7.2 Hz), 6.45 (1H, dd, J=0.6, 9.2 Hz), 7.01–7.06 (1H, m), 7.10–7.15 (2H, m), 7.23 (1H, dd, J=0.6, 2.6 Hz), 7.26–7.30 (1H, m), 7.33 (1H, dd, J=2.6, 9.2 Hz).

Example 17

2-Amino-5-[1-(2-fluoroethyl)-6-oxo-1,6-dihydro-3-pyridinyl]-6-(3-fluorophenyl)-3-methyl-3,4-dihydro-4-pyrimidinone

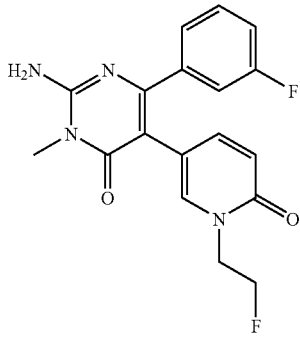

The title compound was obtained in a manner similar to that described for Example 14 from 1-fluoro-2-iodoethane.

$^1$H NMR (400 MHz, CD$_3$OD) δ ppm; 3.48 (3H, s), 4.17 (2H, dt, J=4.8, 26 Hz), 4.53 (2H, dt, J=4.8, 47 Hz), 6.45 (1H, d, J=9.2 Hz), 7.01–7.06 (1H, m), 7.10–7.15 (2H, m), 7.25–7.28 (2H, m), 7.31 (1H, dd, J=2.4, 9.2 Hz).

Example 18

5-(1-allyl-6-oxo-1,6-dihydro-3-pyridinyl)-2-amino-6-(3-fluorophenyl)-3-methyl-3,4-dihydro-4-pyrimidinone

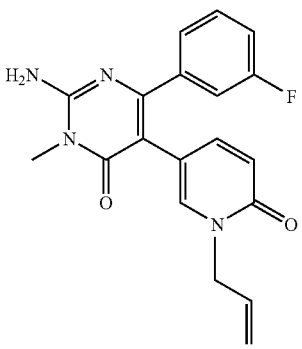

The title compound was obtained in a manner similar to that described for Example 14 from allyl bromide.

$^1$H NMR (400 MHz, CD$_3$OD) δ ppm; 3.48 (3H, s), 4.46 (2H, ddd, J=1.6, 3.2, 5.2 Hz), 4.87–4.90 (1H, m), 5.06 (dd, J=1.2, 10.4 Hz), 5.71–5.81 (1H, m), 6.47 (1H, d, J=9.2 Hz), 7.02–7.07 (1H, m), 7.09–7.14 (2H, m), 7.19 (1H, d, J=2.4 Hz), 7.25–7.31 (1H, m), 7.35 (1H, dd, J=2.4, 9.2 Hz).

Example 19

2-Amino-5-[1-(2-butynyl)-6-oxo-1,6-dihydro-3-pyridinyl]-6-(3-fluorophenyl)-3-methyl-3,4-dihydro-4-pyrimidinone

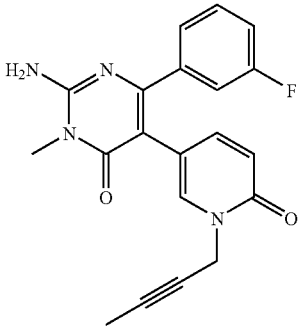

The title compound was obtained in a manner similar to that described for Example 14 from 1-bromo-2-butyne.

$^1$H NMR (400 MHz, CD$_3$OD) δ ppm; 1.78 (3H, t, J=2.4 Hz), 3.49 (3H, s), 4.58 (2H, q, J=2.4 Hz), 6.44 (1H, d, J=9.0 Hz), 7.03–7.18 (3H, m), 7.27–7.31 (1H, m), 7.34 (1H, dd, J=2.2, 9.0 Hz), 7.44 (1H, d, J=2.2 Hz).

Example 20

2-Amino-6-(3-fluorophenyl)-3-methyl-5-(6-oxo-1-phenyl-1,6-dihydro-3-pyridinyl)-3,4-dihydro-4-pyrimidinone

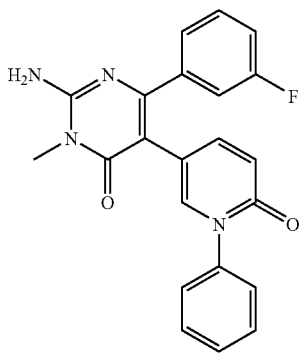

In a flask were placed 2-amino-6-(3-fluorophenyl)-3-methyl-5-(6-oxo-1,6-dihydro-3-pyridinyl)-3,4-dihydro-4-pyrimidinone (40 mg, 0.13 mmol), copper acetate (3 mg, 0.01 mmol), phenylboronic acid (31 mg, 0.26 mmol), pyridine (21 μL, 0.26 mmol) and N,N-dimethylformamide (2 mL), followed by stirring at room temperature for 24 hour. After filtering off the insoluble matters, the filtrate was purified by HPLC, to give the title compound (16 mg). MS m/e (ESI) 389 (MH$^+$).

Example 21

2-Amino-6-(3-fluorophenyl)-3-methyl-5-[6-oxo-1-(3-thienyl)-1,6-dihydro-3-pyridinyl]-3,4-dihydro-4-pyrimidinone

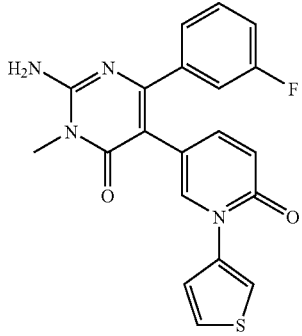

The title compound was obtained in a manner similar to that described for Example 20 from 3-thienylboronic acid.

$^1$H NMR (400 MHz, CD$_3$OD) δ ppm; 3.49 (3H, s), 6.50 (1H, dd, J=0.8, 9.2 Hz), 7.03 (1H, dd, J=1.6, 5.4 Hz), 7.08–7.13 (1H, m), 7.16–7.23 (2H, m), 7.32–7.38 (4H, m), 7.48 (1H, dd, J=3.6, 5.4 Hz).

Example 22

2-Amino-3-ethyl-6-(3-fluorophenyl)-5-(6-methoxy-3-pyridyl)-3,4-dihydro-4-pyrimidinone

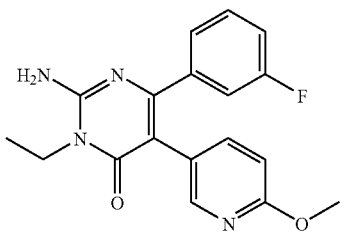

The title compound was obtained in a manner similar to that described for Example 12 from ethyl iodide.

$^1$H NMR (400 MHz, DMSO-d$_6$) δ ppm; 1.17 (3H, t, J=7.0 Hz), 3.77 (3H, s), 4.02 (2H, q, J=7.0 Hz), 6.66 (1H, dd, J=0.8, 8.4 Hz), 6.95–6.98 (1H, m), 7.03–7.10 (2H, m), 7.21–7.26 (1H, m), 7.38–7.40 (3H, m), 7.72 (1H, dd, J=0.8, 2.4 Hz).

Example 23

2-Amino-3-ethyl-6-(3-fluorophenyl)-5-(6-oxo-1,6-dihydro-3-pyridinyl)-3,4-dihydro-4-pyrimidinone

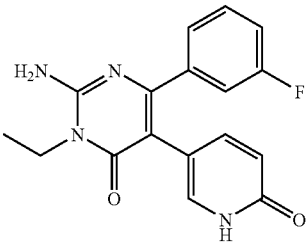

The title compound was obtained in a manner similar to that described for Example 13 from 2-amino-3-ethyl-6-(3-fluorophenyl)-5-(6-methoxy-3-pyridyl)-3,4-dihydro-4-pyrimidinone.

$^1$H NMR (400 MHz, DMSO-d$_6$) δ ppm; 1.17 (3H, t=7.2 Hz), 3.96 (2H, q, J=7.2 Hz), 6.14 (1H, d, J=9.2 Hz), 6.94 (1H, d, J=2.0 Hz), 7.06–7.14 (4H, m), 7.28–7.34 (3H, m).

Example 24

2-Amino-3-ethyl-6-(3-fluorophenyl)-5-(1-methyl-6-oxo-1,6-dihydro-3-pyridinyl)-3,4-dihydro-4-pyrimidinone

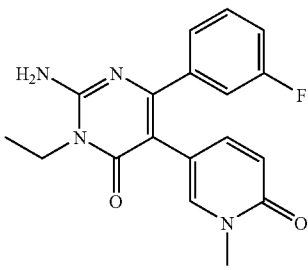

To a solution of 2-amino-3-ethyl-6-(3-fluorophenyl)-5-(6-oxo-1,6-dihydro-3-pyridinyl)-3,4-dihydro-4-pyrimidinone (20 mg, 0.06 mmol) in dimethyl sulfoxide (1 mL) were added potassium carbonate (20 mg, 0.12 mmol) and iodomethane (20 μL, 0.30 mmol), followed by stirring at 50° C. for 16 hours. After filtering off the insoluble matters, the filtrate was purified by HPLC, to give the title compound (4 mg).

$^1$H NMR (400 MHz, CD$_3$OD) δ ppm; 1.32 (3H, t, J=7.2 Hz), 3.47 (3H, s), 4.09 (2H, q, J=7.2 Hz), 6.40 (1H, d, J=9.4 Hz), 7.03–7.08 (1H, m), 7.11 (2H, m), 7.18 (1H, dd, J=2.8, 9.4 Hz), 7.27–7.32 (1H, m), 7.43 (1H, d, J=2.8 Hz).

Example 25

2-Amino-3-ethyl-5-(1-ethyl-6-oxo-1,6-dihydro-3-pyridinyl)-6-(3-fluorophenyl)-3,4-dihydro-4-pyrimidinone

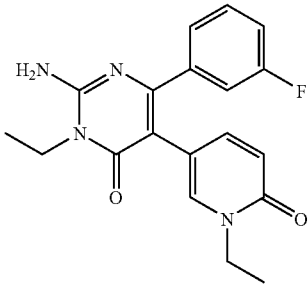

The title compound was obtained in a manner similar to that described for Example 24 from iodoethane.

$^1$H NMR (400 MHz, CD$_3$OD) δ ppm; 1.12 (3H, t, J=7.2 Hz), 1.32 (3H, t, J=7.2 Hz), 3.88 (2H, q, J=7.2 Hz), 4.09 (2H, q, J=7.2 Hz), 6.44 (1H, dd, J=0.4, 9.2 Hz), 7.02–7.07 (1H, m), 7.09–7.15 (2H, m), 7.31 (1H, dd, J=2.4, 9.2 Hz), 7.27–7.29 (2H, m).

Example 26

2-Amino-3-ethyl-6-(3-fluorophenyl)-5-(6-oxo-1-propyl-1,6-dihydro-3-pyridinyl)-3,4-dihydro-4-pyrimidinone

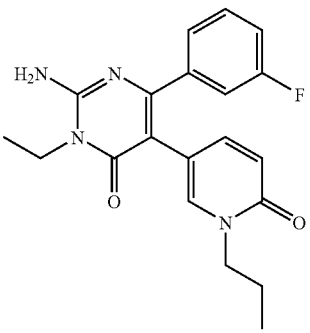

The title compound was obtained in a manner similar to that described for Example 24 from 1-iodopropane.

$^1$H NMR (400 MHz, CD$_3$OD) δ ppm; 0.76 (3H, t, J=7.2 Hz), 1.32 (3H, t, J=6.8 Hz), 1.53 (2H, m), 3.81 (2H, t, J=6.8 Hz), 4.09 (2H, q, J=7.2 Hz), 6.45 (1H, d, J=9.2 Hz), 7.01–7.06 (1H, m), 7.10–7.15 (2H, m), 7.33 (1H, dd, H=2.4, 9.2 Hz), 7.24 (1H, d, J=2.4 Hz), 7.26–7.30 (1H, m).

Example 27

2-Amino-3-ethyl-5-[1-(2-fluoroethyl)-6-oxo-1,6-dihydro-3-pyridinyl]-6-(3-fluorophenyl)-3,4-dihydro-4-pyrimidinone

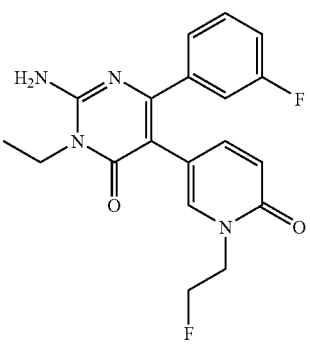

The title compound was obtained in a manner similar to that described for Example 24 from 1-fluoro-2-iodoethane.

$^1$H NMR (400 MHz, CD$_3$OD) δ ppm; 1.32 (3H, t, J=7.2 Hz), 4.09 (2H, q, J=7.2 Hz), 4.17 (2H, dt, J=4.8, 26 Hz), 4.53 (2H, dt, J=4.8, 47 Hz), 6.45 (1H, dd, J=0.8, 9.2 Hz), 7.01–7.06 (1H, m), 7.09–7.16 (2H, m), 7.25–7.30 (2H, m), 7.31 (1H, dd, J=2.4, 9.2 Hz).

Example 28

2-Amino-3-ethyl-6-(3-fluorophenyl)-5-[1-(3-hydroxypropyl)-6-oxo-1,6-dihydro-3-pyridinyl]-3,4-dihydro-4-pyrimidinone

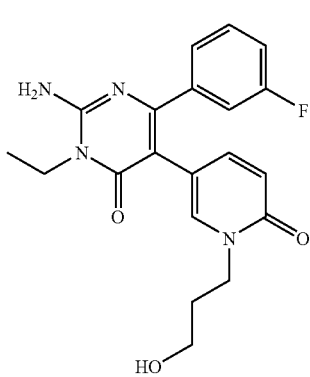

The title compound was obtained in a manner similar to that described for Example 24 from 3-iodopropanol.

$^1$H NMR (400 MHz, CD$_3$OD) δ ppm; 1.32 (3H, t, J=7.2 Hz), 1.70–1.77 (2H, m), 3.41 (2H, t, J=6.0 Hz), 3.96 (2H, t, J=6.8 Hz), 4.09 (2H, q, J=7.2 Hz), 6.44 (1H, d, J=9.2 Hz), 7.02–7.08 (1H, m), 7.10–7.17 (2H, m), 7.26–7.32 (3H, m).

Example 29

5-(1-allyl-6-oxo-1,6-dihydro-3-pyridinyl)-2-amino-3-ethyl-6-(3-fluorophenyl)-3,4-dihydro-4-pyrimidinone

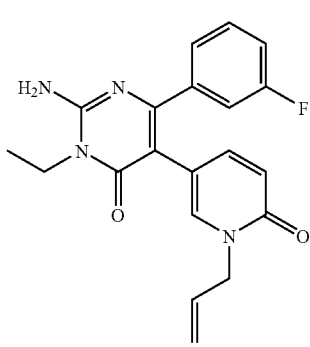

The title compound was obtained in a manner similar to that described for Example 24 from allyl bromide.
MS m/e (ESI) 367 (MH$^+$).

Example 30

2-Amino-5-[1-(2-butynyl)-6-oxo-1,6-dihydro-3-pyridinyl]-3-ethyl-6-(3-fluorophenyl)-3,4-dihydro-4-pyrimidinone

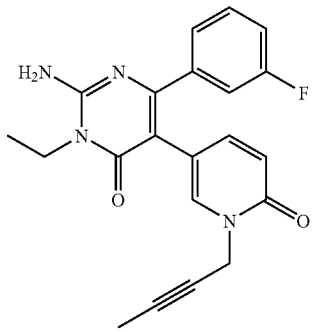

The title compound was obtained in a manner similar to that described for Example 24 from 1-bromo-2-butyne.

$^1$H NMR (400 MHz, CD$_3$OD) δ ppm; 1.32 (3H, t, J=7.2 Hz), 1.78 (3H, t, J=2.4 Hz), 4.09 (2H, q, J=7.2 Hz), 4.58 (2H, q, J=2.4 Hz), 6.44 (1H, dd, J=0.4, 9.2 Hz), 7.03–7.18 (3H, m), 7.27–7.32 (1H, m), 7.34 (1H, dd, J=2.4, 9.2 Hz), 7.44 (1H, dd, J=0.4, 2.4 Hz).

Example 31

2-Amino-5-(1-benzyl-6-oxo-1,6-dihydro-3-pyridinyl)-3-ethyl-6-(3-fluorophenyl)-3,4-dihydro-4-pyrimidinone

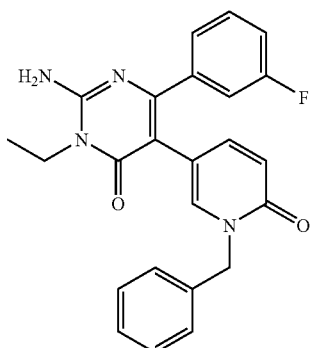

The title compound was obtained in a manner similar to that described for Example 24 from benzyl chloride.

$^1$H NMR (400 MHz, CD$_3$OD) δ ppm; 1.31 (3H, t, J=7.2 Hz), 4.08 (2H, q, J=7.2 Hz), 5.02 (2H, s), 6.51 (1H, d, J=9.2 Hz), 6.97–7.09 (5H, m), 7.17–7.26 (4H, m), 7.29 (1H, d, J=2.4 Hz), 7.41 (1H, dd, J=2.4, 9.2 Hz).

Example 32

2-Amino-3-ethyl-6-(3-fluorophenyl)-5-(6-oxo-1-phenyl-1,6-dihydro-3-pyridinyl)-3,4-dihydro-4-pyrimidinone

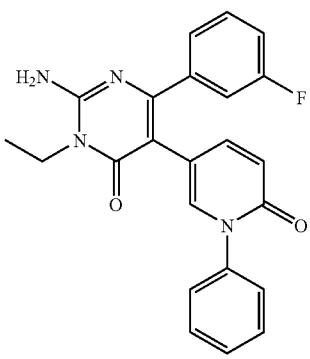

In a flask were placed 2-amino-3-ethyl-6-(3-fluorophenyl)-5-(6-oxo-1,6-dihydro-3-pyridinyl)-3,4-dihydro-4-pyrimidinone (20 mg, 0.06 mmol), copper acetate (3 mg, 0.01 mmol), phenylboronic acid (15 mg, 0.12 mmol), pyridine (11 μL, 0.12 mmol) and N,N-dimethylformamide (1 mL), followed by stirring at room temperature for 24 hours. After filtering off the insoluble matters, the filtrate was purified by HPLC, to give the title compound (8 mg).
MS m/e (ESI) 403 (MH$^+$).

Example 33

2-Amino-3-ethyl-6-(3-fluorophenyl)-5-[6-oxo-1-(3-thienyl)-1,6-dihydro-3-pyridinyl]-3,4-dihydro-4-pyrimidinone

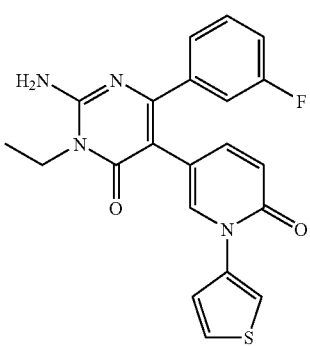

The title compound was obtained in a manner similar to that described for Example 32 from 3-thienylboronic acid.
MS m/e (ESI) 409 (MH$^+$).

Example 34

3-allyl-2-amino-6-(3-fluorophenyl)-5-(6-methoxy-3-pyridyl)-3,4-dihydro-4-pyrimidinone

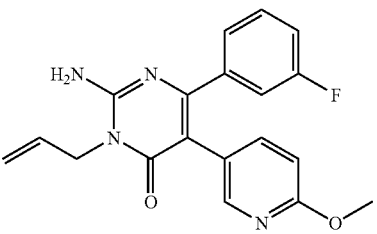

The title compound was obtained in a manner similar to that described for Example 12 from allyl bromide.

$^1$H NMR (400 MHz, DMSO-d$_6$) δ ppm; 3.77 (3H, s), 4.59 (2H, d, J=5.2 Hz), 5.17–5.22 (2H, m), 5.81–5.91 (1H, m), 6.67 (1H, dd, J=0.8, 8.4 Hz), 6.97–7.00 (1H, m), 7.04–7.10 (2H, m), 7.21–7.27 (1H, m), 7.31 (2H, brs), 7.40 (1H, dd, J=2.4, 8.4 Hz), 7.73 (1H, dd, J=0.8, 2.4 Hz).

Example 35

3-allyl-2-amino-6-(3-fluorophenyl)-5-(6-oxo-1,6-dihydro-3-pyridinyl)-3,4-dihydro-4-pyrimidinone

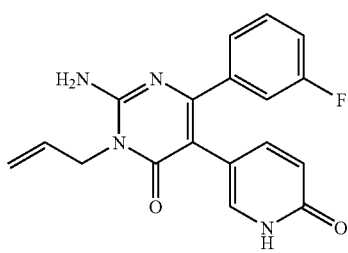

The title compound was obtained in a manner similar to that described for Example 13 from 3-allyl-2-amino-6-(3-fluorophenyl)-5-(6-methoxy-3-pyridyl)-3,4-dihydro-4-pyrimidinone.

$^1$H NMR (400 MHz, DMSO-d$_6$) δ ppm; 4.58 (2H, d, J=5.2 Hz), 5.16–5.21 (2H, m), 5.80–5.90 (1H, m), 6.15 (1H, d, J=9.2 Hz), 6.95 (1H, d, J=2.4 Hz), 7.12 (1H, dd, J=2.4, 9.2 Hz), 7.09–7.16 (3H, m), 7.28–7.34 (3H, m).

Example 36

3-allyl-2-amino-6-(3-fluorophenyl)-5-(1-methyl-6-oxo-1,6-dihydro-3-pyridinyl)-3,4-dihydro-4-pyrimidinone

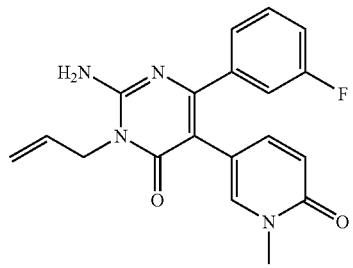

To a solution of 3-allyl-2-amino-6-(3-fluorophenyl)-5-(6-oxo-1,6-dihydro-3-pyridinyl)-3,4-dihydro-4-pyrimidinone in dimethyl sulfoxide were added potassium carbonate (2 equivalents) and iodomethane (4 equivalents), followed by stirring at 50° C. for 16 hours. After filtering off the insoluble matters, the filtrate was purified by HPLC, to give the title compound.

$^1$H NMR (400 MHz, CD$_3$OD) δ ppm; 3.47 (3H, s), 4.70 (2H, ddd, J=1.6, 3.2, 4.8 Hz), 5.20–5.27 (2H, m), 5.94 (1H, ddt, J=4.8, 10.4, 17.2 Hz), 6.39 (1H, d, J=8.8 Hz), 7.03–7.08 (1H, m), 7.14–7.21 (3H, m), 7.26–7.32 (1H, m), 7.45 (1H, d, J=2.4 Hz).

Example 37

3-allyl-2-amino-5-(1-ethyl-6-oxo-1,6-dihydro-3-pyridinyl)-6-(3-fluorophenyl)-3,4-dihydro-4-pyrimidinone

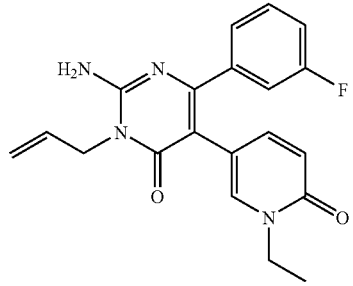

The title compound was obtained in a manner similar to that described for Example 36 from iodoethane.

$^1$H NMR (400 MHz, CD$_3$OD) δ ppm: 1.12 (3H, t, J=7.2 Hz), 3.88 (2H, q, J=7.2 Hz), 4.70 (2H, ddd, J=1.6, 3.6, 5.2 Hz), 5.23 (1H, dd, J=0.8, 10.4 Hz), 5.26 (1H, dd, J=0.8, 17.2 Hz), 5.94 (1H, ddt, J=5.2, 10.4, 17.2 Hz), 6.43 (1H, dd, J=0.8, 8.8 Hz), 7.03–7.08 (1H, m), 7.11–7.18 (2H, m), 7.27–7.31 (2H, m), 7.33 (1H, d, J=2.8 Hz).

Example 38

3-allyl-2-amino-6-(3-fluorophenyl)-5-(6-oxo-1-propyl-1,6-dihydro-3-pyridinyl)-3,4-dihydro-4-pyrimidinone

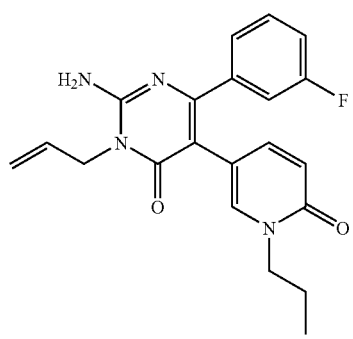

The title compound was obtained in a manner similar to that described for Example 36 from 1-iodopropane.

$^1$H NMR (400 MHz, CD$_3$OD) δ ppm; 0.76 (3H, t, J=7.2 Hz), 1.53 (2H, sex, J=7.2 Hz), 3.82 (2H, t, J=7.2 Hz), 4.70 (2H, ddd, J=2.0, 3.6, 5.0 Hz), 5.20–5.27 (2H, m), 5.94 (1H, ddt, J=5.0, 10.4, 17.2 Hz), 6.44 (1H, dd, J=0.4, 9.4 Hz), 7.02–7.07 (1H, m), 7.12–7.17 (2H, m), 7.26 (1H, dd, J=0.4, 2.6 Hz), 7.26–7.31 (1H, m), 7.33 (1H, dd, J=2.6, 9.4 Hz).

Example 39

3-allyl-2-amino-5-[1-(2-fluoroethyl)-6-oxo-1,6-dihydro-3-pyridinyl]-6-(3-fluorophenyl)-3,4-dihydro-4-pyrimidinone

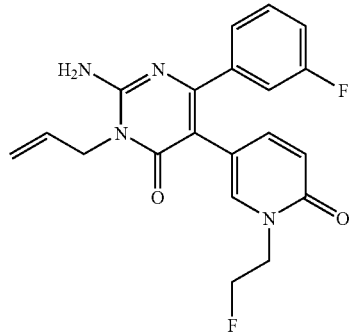

The title compound was obtained in a manner similar to that described for Example 36 from 1-fluoro-2-iodoethane.

$^1$H NMR (400 MHz, CD$_3$OD) δ ppm; 4.17 (2H, dt, J=5.2, 25.6 Hz), 4.53 (2H, dt, J=5.2, 46.8 Hz), 4.70 (2H, ddd, J=1.6, 3.6, 4.8 Hz), 5.21–5.27 (2H, m), 5.90–6.00 (1H, m), 6.45 (1H, dd, J=1.6, 8.0 Hz), 7.01–7.06 (1H, m), 7.11–7.18 (2H, m), 7.25–7.33 (3H, m).

Example 40

3-allyl-2-amino-6-(3-fluorophenyl)-5-[1-(3-hydrox-ypropyl)-6-oxo-1,6-dihydro-3-pyridinyl]-3,4-dihydro-4-pyrimidinone

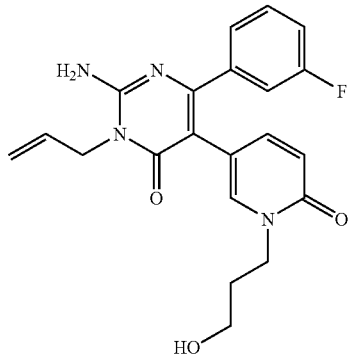

The title compound was obtained in a manner similar to that described for Example 36 from 1-bromo-3-propanol.

$^1$H NMR (400 MHz, CD$_3$OD) δ ppm; 1.74 (2H, quint, J=6.8 Hz), 3.41 (2H, t, J=6.8 Hz), 3.96 (2H, t, J=6.8 Hz), 4.70 (2H, ddd, J=1.6, 3.6, 5.0 Hz), 5.23 (1H, dd, J=1.2, 15.6 Hz), 5.27 (1H, dd, J=1.2, 10.4 Hz), 5.94 (1H, ddt, J=5.0, 10.4, 15.6 Hz), 6.44 (1H, dd, J=0.8, 8.8 Hz), 7.03–7.08 (1H, m), 7.12–7.19 (2H, m), 7.28–7.32 (3H, m).

Example 41

3-allyl-5-(1-allyl-6-oxo-1,6-dihydro-3-pyridinyl)-2-amino-6-(3-fluorophenyl)-3,4-dihydro-4-pyrimidinone

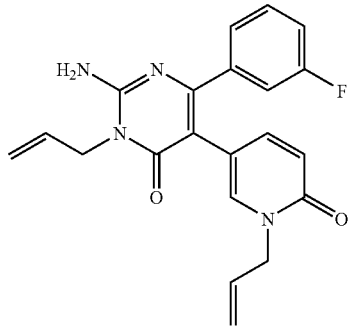

The title compound was obtained in a manner similar to that described for Example 36 from allyl bromide.

$^1$H NMR (400 MHz, CD$_3$OD) δ ppm; 4.46 (2H, ddd, J=1.2, 2.8, 5.2 Hz), 4.69 (2H, ddd, J=1.6, 3.2, 5.2 Hz), 4.86–4.90 (1H, m), 5.07 (1H, dd, J=1.6, 10.4 Hz), 5.22 (1H, dd, J=0.8, 15.6 Hz), 5.26 (1H, dd, J=0.8, 10.4 Hz), 5.76 (1H, ddt, J=5.2, 10.4, 15.6 Hz), 5.94 (1H, ddt, J=5.2, 10.4, 15.6 Hz), 6.46 (1H, d, J=9.2 Hz), 7.02–7.07 (1H, m), 7.11–7.16 (2H, m), 7.21 (1H, d, J=2.4 Hz), 7.26–7.32 (1H, m), 7.35 (1H, dd, J=2.4, 9.2 Hz).

Example 42

3-allyl-2-amino-5-[1-(2-butynyl)-6-oxo-1,6-dihydro-3-pyridinyl]-6-(3-fluorophenyl)-3,4-dihydro-4-pyrimidinone

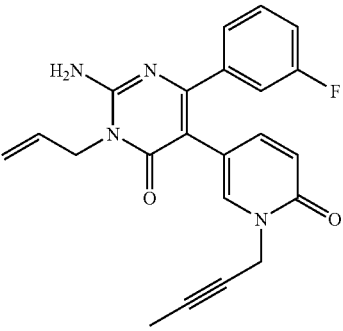

The title compound was obtained in a manner similar to that described for Example 36 from 1-bromo-2-butyne.

$^1$H NMR (400 MHz, CD$_3$OD) δ ppm; 1.78 (3H, t, J=2.4 Hz), 4.58 (2H, q, J=2.4 Hz), 4.70 (2H, ddd, J=2.0, 3.6, 5.2 Hz), 5.21–5.28 (2H, m), 5.95 (1H, ddt, J=5.2, 10.4, 15.6 Hz), 6.44 (1H, dd, J=0.4, 9.2 Hz), 7.04–7.09 (1H, m), 7.16–7.20 (2H, m), 7.27–7.33 (1H, m), 7.35 (1H, dd, J=2.4, 9.2 Hz), 7.46 (1H, dd, J=0.4, 2.4 Hz).

Example 43

3-allyl-2-amino-5-(1-benzyl-6-oxo-1,6-dihydro-3-pyridinyl)-6-(3-fluorophenyl)-3,4-dihydro-4-pyrimidinone

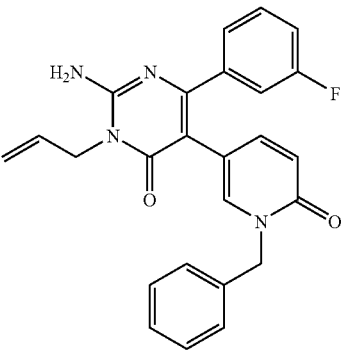

The title compound was obtained in a manner similar to that described for Example 36 from benzyl chloride.

$^1$H NMR (400 MHz, CD$_3$OD) δ ppm; 4.69 (2H, ddd, J=2.0, 3.2, 4.8 Hz), 5.02 (2H, s), 5.22 (1H, J=1.2, 15.6 Hz), 5.25 (1H, dd, J=1.2, 10.4 Hz), 5.93 (1H, ddt, J=4.8, 10.4, 15.6 Hz), 6.50 (1H, d, J=9.2 Hz), 6.97–7.11 (5H, m), 7.11–7.26 (4H, m), 7.31 (1H, d, J=2.4 Hz), 7.41 (1H, dd, J=2.4, 9.2 Hz).

Example 44

3-allyl-2-amino-6-(3-fluorophenyl)-5-(6-oxo-1-phenyl-1,6-dihydro-3-pyridinyl)-3,4-dihydro-4-pyrimidinone

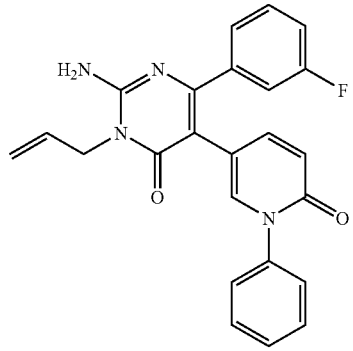

In a flask were placed 3-allyl-2-amino-6-(3-fluorophenyl)-5-(6-oxo-1,6-dihydro-3-pyridinyl)-3,4-dihydro-4-pyrimidinone (20 mg, 0.06 mmol), copper acetate (3 mg, 0.01 mmol), phenylboronic acid (15 mg, 0.12 mmol), pyridine (11 μL, 0.12 mmol) and N,N-dimethylformamide (1 mL), followed by stirring at room temperature for 24 hours. After filtering off the insoluble matters by filtration, the filtrate was purified by HPLC, to give the title compound (8 mg).

MS m/e (ESI) 415 (MH+).

Example 45

3-allyl-2-amino-6-(3-fluorophenyl)-5-[6-oxo-1-(3-thienyl)-1,6-dihydro-3-pyridinyl]-3,4-dihydro-4-pyrimidinone

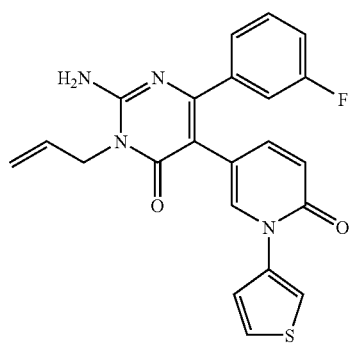

The title compound was obtained in a manner similar to that described for Example 44 from 3-thienylboronic acid.

MS m/e (ESI) 421 (MH+).

Example 46

2-Amino-6-(2-furyl)-5-(6-methoxy-3-pyridyl)-3,4-dihydro-4-pyrimidinone

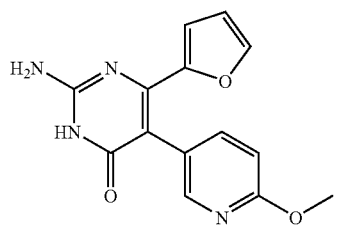

The title compound was obtained by reacting in a manner similar to that described for the Method 2 of Example 1 "from (E)-3-(2-furyl)-2-(6-methoxy-3-pyridyl)-2-propenenitrile", and then purifying by HPLC.

$^1$H NMR (400 MHz, CD$_3$OD) δ ppm; 3.98 (3H, s), 6.23 (1H, dd, J=0.8, 3.6 Hz), 6.53 (1H, dd, J=1.6, 3.6 Hz), 6.96 (1H, dd, J=0.8, 8.8 Hz), 7.63 (1H, dd, J=2.4, 8.8 Hz), 7.74 (1H, dd, J=0.8, 1.6 Hz), 8.03 (1H, dd, J=0.8, 2.4 Hz).

The compounds represented by the above formula (I) according to the present invention are useful as an adenosine receptor (A$_1$, A$_{2A}$, A$_{2B}$ or A$_3$ receptor) antagonist and are specifically useful as an A$_{2B}$ receptor antagonist. Test examples demonstrating the efficacy of the compounds of the present invention as a medicament will be described below.

Test Example 1

Measurement of the Binding Ability to Adenosine A$_1$ Receptor

A human adenosine A$_1$ receptor cDNA was expressed in excess in CHOK1 cells, and this membrane sample was suspended at a protein concentration of 66.7 μg/ml in 20 mM HEPES buffer, pH 7.4 (10 mM MgCl$_2$, 100 mM NaCl). To 0.45 ml of this membrane sample suspension were added 0.025 ml of 60 nM tritium-labeled chlorocyclopentyl adenosine ($^3$H—CCPA, from NEN Ltd.) and 0.025 ml of test compound. This mixture was left at 30° C. for 120 minutes, filtered rapidly under suction through a glass fiber filter (GF/B, from Whatman), and immediately washed twice with 5 ml of 50 mM water-cooled Tris-HCl buffer. Thereafter, the glass fiber filter was transferred to a vial, scintillator was added thereto, and the radioactivity on the filter was measured by a liquid scintillation counter. The inhibition of binding of $^3$H-CCPA to A$_1$ receptor by the test compound was determined using the following formula, and from this inhibition, 50% inhibition concentration (IC$_{50}$) was calculated (the following equation).

Inhibition (%)=[1−{(binding in the presence of the test compound−non-specific binding)/(total binding−non-specific binding)}]×100

In the above formula, the total binding means $^3$H-CCPA-bound radioactivity in the absence of the test compound; the nonspecific binding means $^3$H-CCPA-bound radioactivity in the presence of 100 μM RPIA ([R]-[1-methyl-2-phenylethyl] adenosine); and the binding in the presence of the test compound means $^3$H-CCPA-bound radioactivity in the presence of the test compound at predetermined concentrations.

The inhibition constant (Ki value) in the table was determined from the formula of Cheng-Prusoff.

Test Example 2

Measurement of the Binding Ability to Adenosine $A_{2A}$ Receptor

An experiment of inhibition of binding to adenosine $A_{2A}$ receptor was conducted using a membrane sample (Receptor Biology Inc.) where an adenosine $A_{2A}$ receptor cDNA was expressed in excess. This membrane sample was suspended at a protein concentration of 22.2 µg/ml in 20 mM HEPES buffer, pH 7.4 (10 mM $MgCl_2$ and 100 mM NaCl). To 0.45 ml of this membrane sample suspension were added 0.025 ml of 500 nM tritium-labeled 2-p-[2-carboxyethyl]phenetylamino-5'-N-ethylarboxyamide adenosine ($^3$H-CGS21680, from NEN) and 0.025 ml of test compound. This mixture was left at 25° C. for 90 minutes, filtered rapidly under suction through a glass fiber filter (GF/B, from Whatman), and immediately washed twice with 5 ml of 50 mM ice-cooled Tris-HCl buffer. Thereafter, the glass fiber filter was transferred to a vial, scintillator was added thereto, and the radioactivity on the filter was measured by a liquid scintillation counter. The inhibition of binding of $^3$H-CGS21680 to $A_{2A}$ receptor by the test compound was determined using the following formula, and from this inhibition, 50% inhibition concentration ($IC_{50}$) was calculated.

Inhibition (%)=[1−{[(binding in the presence of the test compound)−(nonspecific binding)]/[(total binding)−(nonspecific binding)]}×100

Here, the total binding means $^3$H-CGS21680-bound radioactivity in the presence of the test compound; the nonspecific binding means $^3$H-CGS21680-bound radioactivity in the presence of 100 µM RPIA; and the binding in the presence of the test compound means $^3$H-CGS21680-bound radioactivity in the absence of the test compound at predetermined concentrations. The inhibition constant (Ki value) in the table was determined from the formula of Cheng-Prusoff.

Test Example 3

Experiment of Inhibition of NECA-Stimulated Production of cAMP in Adenosine $A_{2B}$ Receptor-Expressing Cells CHOK1 cells where human adenosine $A_{2B}$ receptor had been expressed in excess were plated onto a 24-well plate at a density of $1.5\times10^5$ cells/well, cultured overnight, and used in the experiment. The degree of inhibitory effect of the test compound on the amount of cAMP produced by stimulation with 30 nM 5'-N-ethylcarboxyamide adenosine (NECA from Sigma) was evaluated in terms of affinity for $A_{2B}$ receptor. That is, the adhering cells were washed twice with 2 ml/well Krebs-Ringer buffer solution (containing 0.1% BSA; pH 7.4) and pre-incubated for 30 minutes in a volume of 0.5 ml/well. Then, a mixed solution containing NECA and the test compound was added in a volume of 0.1 ml/well in the presence of a phosphodiesterase inhibitor Ro-20-1724 (a product of RBI). After pre-incubation for 15 minutes, the reaction was terminated with 0.1 N HCl in a volume of 300 µl/well. Measurement of intracellular cAMP was carried out using a cAMP enzyme immunoassay kit produced by Amersham. The inhibition of NECA-stimulated production of cAMP by the test compound was determined using the following equation:

Inhibition (%)=[1−{(amount of cAMP in the coexistence of NECA and the test compound-amount of cAMP in only the Krebs-Ringer buffer solution)/(amount of cAMP upon stimulation with NECA only-amount of cAMP in only the Krebs-Ringer buffer solution)}]×100

The ability of the compound according to the present invention to bind to or the ability to antagonize adenosine receptor are as follows.

TABLE 1

|  | $K_1$(nM) | $K_1$(nM) | $IC_{50}$(nM) |
| --- | --- | --- | --- |
| Test Compound | $A_1$ | $A_{2A}$ | $A_{2B}$ |
| Example 2 | 1108 | 345 | 256 |
| Example 7 | 966 | 493 | 71 |

The compounds according to the present invention or salts thereof have an excellent inhibitory action against the adenosine receptors.

Test Example 4

Evaluation of Defecation-Promoting Action

The defecation-promoting action of the adenosine $A_{2B}$ receptor-inhibiting compound which was identified by measuring the binding ability and inhibitory ability thereof to the adenosine receptor in Test Examples 1 to 3, a salt thereof, a solvate of them, or a pharmaceutical composition containing it can be evaluated on the basis of the following method. That is, SD IGS rats (6 weeks-old, from Charles River) were placed in cages (3 animals/cage) and preliminarily allowed food and water ad libitum and raised for 1 week. Then, a tared water-absorbing sheet was placed below each cage, and the animals were fasted but allowed water ad libitum throughout the experiment. After 1.5 hours, the fecal pellets were collected from each cage and observed for abnormality before the experiment. The compound suspended or dissolved in 0.5% (w/v) methyl cellulose (MC) was orally administered in a volume of 5 ml/kg. On one hand, 0.5% (w/v) MC only was orally given to the control group. After administration of the compound, the rats were returned to the cage provided with a new water-absorbing sheet, and 90 minutes after the administration, the fecal pellets on the water-absorbing sheet were collected from each cage, and the external appearance was observed, and then counted and weighed. The number of fecal pellets is expressed per each cage.

The compounds according to the present invention, a salt thereof or solvates of them have an excellent defecation-promoting action.

We claim:

1. A compound represented by the following formula (I), a salt thereof or a solvate thereof:

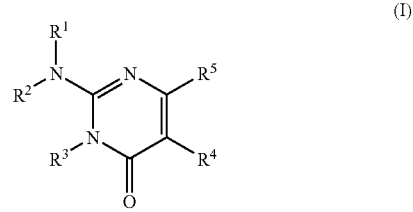

(I)

wherein in the formula, $R^1$ and $R^2$ are the same as or different from each other and each represents a hydrogen atom, an alkyl group having one to six carbon atoms which may be substituted, an alkenyl group having two to six carbon atoms which may be substituted, an alkynyl group having two to six carbon atoms which may be substituted, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic cyclic hydrocarbon group having six to fourteen carbon atoms which may be substituted, a 5 to 14-membered aromatic heterocyclic group which may be substituted, an acyl group having one to six carbon atoms which may be substituted or an alkylsulfonyl group having one to six carbon atoms which may be substituted;

$R^3$ represents a hydrogen atom, an alkyl group having one to six carbon atoms which may be substituted, an alkenyl group having two to six carbon atoms which may be substituted or an alkynyl group having two to six carbon atoms which may be substituted;

$R^4$ represents a pyridyl which may be substituted or a pyridone group which may be substituted; and $R^5$ represents an aromatic cyclic hydrocarbon group having six to fourteen carbon atoms which may be substituted or a 5 to 14-membered aromatic heterocyclic group which may be substituted.

2. The compound according to claim 1, a salt thereof or a solvate thereof, wherein $R^4$ is 4-pyridyl group which may be substituted.

3. The compound according to claim 1 or 2, a salt thereof or a solvate thereof, wherein $R^4$ is represented by the formula:

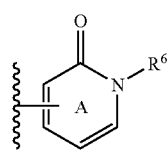

(II)

wherein $R^6$ represents a group selected from the following Substituent Group a; and the ring A may be substituted with one to four groups selected from the following Substituent Group a:

<Substituent Group a> the group consisting of a hydrogen atom, a halogen atom, a hydroxyl group, a nitro group, a cyano group, an alkyl group having one to six carbon atoms which may be substituted, an alkenyl group having two to six carbon atoms which may be substituted, an alkynyl group having two to six carbon atoms which may be substituted, an alkoxy group having one to six carbon atoms which may be substituted, an alkenyloxy group having two to six carbon atoms which may be substituted, an alkynyloxy group having two to six carbon atoms which may be substituted, an alkylthio group having one to six carbon atoms which may be substituted, an alkenylthio group having two to six carbon atoms which may be substituted, an alkynylthio group having two to six carbon atoms which may be substituted, an aliphatic acyl group having two to seven carbon atoms, a carbamoyl group which may be substituted, an arylacyl group, a heteroarylacyl group, an amino group which may be substituted, an alkylsulfonyl group having one to six carbon atoms which may be substituted, an alkenylsulfonyl group having two to six carbon atoms which may be substituted, an alkynylsulfonyl group having two to six carbon atoms which may be substituted, an alkylsulfinyl group having one to six carbon atoms which may be substituted, an alkenylsulfinyl group having two to six carbon atoms which may be substituted, an alkynylsulfinyl group having two to six carbon atoms which may be substituted, a formyl group, a cycloalkyl group having three to eight carbon atoms which may be substituted, a cycloalkenyl group having three to eight carbon atoms which may be substituted, a 5 to 14-membered non-aromatic heterocyclic group which may be substituted, an aromatic cyclic hydrocarbon group having six to fourteen carbon atoms which may be substituted and a 5 to 14-membered aromatic heterocyclic group which may be substituted.

4. The compound according to claim 3, a salt thereof or a solvate thereof, wherein $R^4$ is represented by the formula:

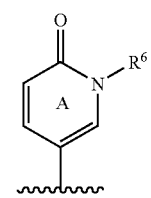

(III)

or the formula:

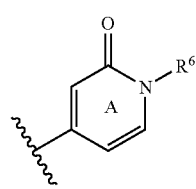

(IV)

wherein in the formulae (III) and (IV), $R^6$ represents a group selected from Substituent Group a as defined in claim 3; and the ring A represents a nitrogen-containing 6-membered ring which may be substituted with one to four groups selected from the above mentioned Substituent Group a.

5. The compound according to claim 1 or 2, a salt thereof or a solvate thereof, wherein $R^4$ is 4-pyridyl group which may be substituted with one or two substituent(s).

6. The compound according to claim 1, a salt thereof or a solvate thereof, wherein $R^1$ and/or $R^2$ is a hydrogen atom, an alkyl group which may be substituted, or an acyl group having one to six carbon atoms which may be substituted.

7. The compound according to claim 1, a salt thereof or a solvate thereof, wherein $R^5$ is phenyl group, pyrrolyl group, pyridyl group, pyridazinyl group, pyrimidinyl group, pyrazinyl group, thienyl group, thiazolyl group, furyl group, naphthyl group, quinolinyl group, isoquinolinyl group, phthalazinyl group, naphthyridinyl group, indolyl group or isoindolyl group, each of which may be substituted.

8. A pharmaceutical composition comprising
the compound according to claim 1, a salt thereof or a solvate thereof; and
a pharmaceutically acceptable carrier.

9. The composition according to claim 8, which is an adenosine receptor antagonist.

10. The composition according to claim 8, which is an adenosine $A_2$ receptor antagonist.

11. The composition according to claim 8, which is adenosine $A_{2B}$ receptor antagonist.

12. A method for promoting defecation, which comprises administering a pharmacologically effective amount of the compound of claim 1, a salt thereof or a solvate thereof to a patient in need thereof.

13. A method for treating or improving irritable bowel syndrome, constipation accompanying irritable bowel syndrome, organic constipation, constipation accompanying enteroparalytic ileus, constipation accompanying congenital digestive tract dysfunction or constipation accompanying ileus, said method comprising:
administering a pharmaceutically effective amount of the compound of claim 1, a salt thereof or a solvate of them to a patient in need thereof.

14. The method according to claim 13, said administration step is to evacuate intestinal tracts at the time of examination of digestive tracts or before and after an operation.

15. The method according to claim 13, wherein said constipation is functional constipation.

16. A method for promoting defecation, which comprises administering the pharmaceutical composition of claim 8 to a patient in need thereof.

17. A method for treating or improving irritable bowel syndrome, constipation accompanying irritable bowel syndrome, organic constipation, constipation accompanying enteroparalytic ileus, constipation accompanying congenital digestive tract dysfunction or constipation accompanying ileus, said method comprising:
administering the pharmaceutical composition of claim 8 to a patient in need thereof.

18. The method according to claim 17, said administration step is to evacuate intestinal tracts at the time of examination of digestive tracts or before and after an operation.

19. The method according to claim 17, wherein said constipation is functional constipation.

* * * * *